US008835147B2

(12) United States Patent
Moon et al.

(10) Patent No.: US 8,835,147 B2
(45) Date of Patent: Sep. 16, 2014

(54) CELLULAR PRODUCTION OF GLUCARIC ACID THROUGH RECOMBINANT EXPRESSION OF URONATE DEHYDROGENASE AND MYO-INOSITOL OXYGENASE

(75) Inventors: Tae Seok Moon, San Francisco, CA (US); Sang-Hwal Yoon, Buyeo (KR); Kristala Lanett Jones Prather, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 473 days.

(21) Appl. No.: 12/935,983

(22) PCT Filed: Apr. 3, 2009

(86) PCT No.: PCT/US2009/002111
§ 371 (c)(1),
(2), (4) Date: Dec. 21, 2010

(87) PCT Pub. No.: WO2009/145838
PCT Pub. Date: Mar. 12, 2009

(65) Prior Publication Data
US 2011/0124065 A1    May 26, 2011

Related U.S. Application Data

(60) Provisional application No. 61/042,502, filed on Apr. 4, 2008.

(51) Int. Cl.
| | |
|---|---|
| *C12N 9/04* | (2006.01) |
| *C12N 15/63* | (2006.01) |
| *C12N 1/20* | (2006.01) |
| *C12P 33/02* | (2006.01) |
| *C12P 21/00* | (2006.01) |
| *C12N 15/82* | (2006.01) |
| *C12P 7/58* | (2006.01) |
| *C12N 9/90* | (2006.01) |
| *C12P 19/02* | (2006.01) |
| *C12P 19/00* | (2006.01) |
| *C12N 9/02* | (2006.01) |

(52) U.S. Cl.
CPC ........ *C12N 15/8245* (2013.01); *C12N 15/8243* (2013.01); *C12P 7/58* (2013.01); *C12N 9/90* (2013.01); *C12N 9/0006* (2013.01); *C12P 19/02* (2013.01); *C12P 19/00* (2013.01); *C12N 9/0069* (2013.01)
USPC ..................... 435/190; 435/320.1; 435/252.3; 435/61; 435/71.1; 435/70.1

(58) Field of Classification Search
None
See application file for complete search history.

(56) References Cited

U.S. PATENT DOCUMENTS 7,326,549 B2    2/2008 Schroeder et al.

FOREIGN PATENT DOCUMENTS

| WO | WO9729194 | * | 8/1997 | ............ C12N 15/53 |
|---|---|---|---|---|
| WO | WO 02/074926 A2 | | 9/2002 | |

OTHER PUBLICATIONS

Iranpour et al, Characterizing uronate dehydrogenase from *P. syringae* as a step towards expressing a retro-biosynthetically derived glucaric acid pathway in *E. coli*. Master's Thesis Department of Chemical Engineering. MITLibraries Jun. 13, 2006.*
Williams et al, Design, synthesis and expression of a human interleukin-2 gene incorporating the codon usage bias found in highly expressed *Escherichia coli* genes. Nucleic Acids Res. Nov. 25, 1988; 16(22): 10453-10467.*
DE19604798 English Translation; Equivalent to WO199729194 Matts et al Aug. 1997.*
NCBI Acc# DAA06455.1 from Yoon et al, J Bacteriol. Mar. 2009;191(5):1565-73. doi: 10.1128/JB.00586-08. Epub Dec. 5, 2008. Alignment with SEQ ID No. 26.*
Yoon et al, Cloning and characterization of uronate dehydrogenases from two pseudomonads and *Agrobacterium tumefaciens* strain C58. J Bacteriol. Mar. 2009;191(5):1565-73. doi: 10.1128/JB.00586-08. Epub Dec. 5, 2008.*
NCBI Acc# DAA06455.1 from Yoon et al, J Bacteriol. Mar. 2009;191(5):1565-73. doi: 10.1128/JB.00586-08. Epub Dec. 5, 2008.*
GenBank Submission; Accession No. EU377538.1; Yoon et al.; Feb. 18, 2009. 1 page.
GenBank Submission; Accession No. NP357458.2; Goodner et al.; Jan. 20, 2012. 2 pages.
GenBank Submission; Accession No. NP743331.1; Nelson et al.; Mar. 28, 2012. 2 pages.
GenBank Submission; Accession No. Q7CRQ0; Goodner et al.; Oct. 31, 2006. 1 page.
GenBank Submission; Accession No. Q888H1; Buell et al.; Nov. 14, 2006. 1 page.
GenBank Submission; Accession No. Q88NN6; Nelson et al.; Oct. 31, 2006. 1 page.
Arner et al., Molecular cloning, expression, and characterization of myo-inositol oxygenase from mouse, rat, and human kidney. Biochem Biophys Res Commun. Nov. 26, 2004;324(4):1386-92.
Arner et al., myo-Inositol oxygenase: molecular cloning and expression of a unique enzyme that oxidizes myo-inositol and D-chiro-inositol. Biochem J. Dec. 1, 2001;360(Pt2):313-20.
Ashwell et al., A new pathway of uronic acid metabolism. Biochim Biophys Acta. Oct. 1958;30(1):186-7.
Bailey. Toward a science of metabolic engineering. Science. Jun. 21, 1991;252(5013):1668-75.
Bateman et al., Purification and properties of uronate dehydrogenase from *Pseudomonas syringae*. Arch Biochem Biophys. Jan. 1970;136(1):97-105.
Benner, Synthetic biology: Act natural. Nature. Jan. 9, 2003;421(6919):118.

(Continued)

*Primary Examiner* — Sheridan Swope
(74) *Attorney, Agent, or Firm* — Wolf, Greenfield & Sacks, P.C.

(57) ABSTRACT

The invention relates to the production of glucuronic and glucaric acid in cells through recombinant expression of myo-inositol 1-phosphate synthase, myo-inositol oxygenase and uronate dehydrogenase. Cloning and characterization of the gene encoding uronate dehydrogenase is also disclosed.

27 Claims, 15 Drawing Sheets

(56) References Cited

OTHER PUBLICATIONS

Benner et al., Synthetic biology. Nat Rev Genet. Jul. 2005;6(7):533-43.

Bentley et al., Plasmid-encoded protein: the principal factor in the "metabolic burden" associated with recombinant bacteria. Biotechnol Bioeng. Mar. 25, 1990;35(7):668-81.

Birnbaum et al., Plasmid presence changes the relative levels of many host cell proteins and ribosome components in recombinant Escherichia coli. Biotechnol Bioeng. Apr. 5, 1991;37(8):736-45.

Buell et al., The complete genome sequence of the Arabidopsis and tomato pathogen Pseudomonas syringae pv. tomato DC3000. Proc Natl Acad Sci U S A. Sep. 2, 2003;100(18):10181-6. Epub Aug. 19, 2003.

Chang et al., D-glucaric acid and galactaric acid catabolism by Agrobacterium tumefaciens. J Bacteriol. Apr. 1970;102(1):85-96.

Chang et al., Hexuronic acid dehydrogenase of Agrobacterium tumefaciens. J Bacteriol. Sep. 1969;99(3):667-73.

Charalampous et al., Biochemical studies on inositol. IV. Conversion of inositol to glucuronic acid by rat kidney extracts. J Biol Chem. Sep. 1957;228(1):1-13.

Charalampous, Biochemical studies on inositol. V. Purification and properties of the enzyme that cleaves inositol to D-glucuronic acid. J Biol Chem. Feb. 1959;234(2):220-7.

Cynkin et al., Uronic acid metabolism in bacteria. IV. Purification and properties of 2-keto-3-deoxy-D-gluconokinase in Escherichia coli. J Biol Chem. Jun. 1960;235:1576-9.

Dahiyat et al., De novo protein design: fully automated sequence selection. Science. Oct. 3, 1997;278(5335):82-7.

Dean-Johnson et al., Biosynthesis of inositol in yeast. Primary structure of myo-inositol-1-phosphate synthase (EC 5.5.1.4) and functional analysis of its structural gene, the INO1 locus. J Biol Chem. Jan. 15, 1989;264(2):1274-83.

Duff, Calcium-D-glucarate. Altern Med Rev. 2002;7(4):336-9.

Farmer et al., Aldohexuronic acid catabolism by a soil Aeromonas. J Bacteriol. Jan. 1969;97(1):97-106.

Goodner et al., Genome sequence of the plant pathogen and biotechnology agent Agrobacterium tumefaciens C58. Science. Dec. 14, 2001;294(5550):2323-8.

Hansen et al., Synthesis of 1,2,3,4-tetrahydroxybenzene from d-glucose: Exploiting myo-inositol as a precursor to aromatic chemicals. J Am Chem Soc. 1999;121(15):3799-800.

Hoffmann et al., Understanding oligomerization in 3alpha-hydroxysteroid dehydrogenase/carbonyl reductase from Comamonas testosteroni: an in silico approach and evidence for an active protein. J Biotechnol. Mar. 30, 2007;129(1):131-9. Epub Dec. 5, 2006.

Hubbard et al., Evolution of enzymatic activities in the enolase superfamily: characterization of the (D)-glucarate/galactarate catabolic pathway in Escherichia coli. Biochemistry. Oct. 13, 1998;37(41):14369-75.

Hugouvieux-Cotte-Pattat et al., Hexuronate catabolism in Erwinia chrysanthemi. J Bacteriol. Mar. 1987;169(3):1223-31.

Hugouvieux-Cotte-Pattat et al., Molecular characterization of the Erwinia chrysanthemi kdgK gene involved in pectin degradation. J Bacteriol. Apr. 1994;176(8):2386-92.

Hugouvieux-Cotte-Pattat et al., Regulation of pectinolysis in Erwinia chrysanthemi. Annu Rev Microbiol. 1996;50:213-57.

Hugouvieux-Cotte-Pattat et al., Two transporters, TogT and TogMNAB, are responsible for oligogalacturonide uptake in Erwinia chrysanthemi 3937. Mol Microbiol. Sep. 2001;41(5):1125-32.

Ibert et al., Determination of the side-products formed during the nitroxide-mediated bleach oxidation of glucose to glucaric acid. Carbohydr Res. Jun. 5, 2002;337(11):1059-63.

Jones et al., Low-copy plasmids can perform as well as or better than high-copy plasmids for metabolic engineering of bacteria. Metab Eng. Oct. 2000;2(4):328-38.

Khosla et al., Metabolic engineering for drug discovery and development. Nat Rev Drug Discov.Dec. 2003;2(12):1019-25.

Kilgore et al., Catabolism of galacturonic and glucuronic acids by Erwinia carotovora. J Biol Chem. Sep. 1959;234:2227-35.

Kilgore et al., Uronate oxidation by phytopathogenic pseudomonads. Nature. May 16, 1959;183(4672):1412-3.

Kleiger et al., GXXXG and GXXXA motifs stabilize FAD and NAD(P)-binding Rossmann folds through C(alpha)-H . . . O hydrogen bonds and van der waals interactions. J Mol Biol. Oct. 11, 2002;323(1):69-76.

Li et al., Computational discovery of biochemical routes to specialty chemicals. Chem Eng Sci. Nov.-Dec. 2004;59(22-3):5051-60.

Marsh, Biosynthesis of D-glucaric acid in mammals: a free-radical mechanism? Carbohydr Res. Sep. 15, 1986;153(1):119-31.

Martin et al., Engineering a mevalonate pathway in Escherichia coli for production of terpenoids. Nat Biotechnol. Jul. 2003;21(7):796-802. Epub Jun. 1, 2003.

Mata-Gilsinger et al., Physical mapping of the exuT and uxaC operators by use of exu plasmids and generation of deletion mutants in vitro. J Bacteriol. Sep. 1983;155(3):973-82.

Matsuhisa et al., Inositol monophosphatase activity from the Escherichia coli suhB gene product. J Bacteriol. Jan. 1995;177(1):200-5.

Mavrovouniotis, Estimation of standard Gibbs energy changes of biotransformations. J Biol Chem. Aug. 5, 1991;266(22):14440-5.

McRorie et al., Alduronic acid metabolism by bacteria. J Bacteriol. Feb. 1959;77(2):212-6.

McRorie et al., Glucuronate metabolism by Aerobacter aerogenes. Nature. Nov. 29, 1958;182(4648):1504-5.

Merbouh et al., Facile nitroxide-mediated oxidations of D-glucose to D-glucaric acid. Carbohydr Res. Nov. 1, 2001;336(1):75-8.

Moon et al. Production of glucaric acid from a synthetic pathway in recombinant Escherichia coli. Appl Environ Microbiol. Feb. 2009;75(3):589-95. Epub Dec. 5, 2008.

Moon et al., Toward microbial synthesis of glucaric acid. Am Chem Soc. The National Meeting Aug. 19-23, 2007;234:BiOT-148.

Nakamura et al., Metabolic engineering for the microbial production of 1,3-propanediol. Curr Opin Biotechnol. Oct. 2003;14(5):454-9.

Nelson et al., Complete genome sequence and comparative analysis of the metabolically versatile Pseudomonas putida KT2440. Environ Microbiol. Dec. 2002;4(12):799-808.

Niu et al., Microbial synthesis of the energetic material precursor 1,2,4-butanetriol. J Am Chem Soc. Oct. 29, 2003;125(43):12998-9.

Payne et al., Glucuronate isomerase from Serratia marcescens. Biochim Biophys Acta. Aug. 1958;29(2):466-7.

Portalier et al., Studies of mutations in the uronic isomerase and altronic oxidoreductase structural genes of Escherichia coli K 12 (author's transl). Mol Gen Genet. 1974;128(4):301-19. French.

Postma et al., Phosphoenolpyruvate:carbohydrate phosphotransferase systems of bacteria. Microbiol Rev. Sep. 1993;57(3):543-94.

Reddy et al., myo-Inositol oxygenase from hog kidney. I. Purification and characterization of the oxygenase and of an enzyme complex containing the oxygenase and D-glucuronate reductase. J Biol Chem. Aug. 25, 1981;256(16):8510-8.

Reddy et al., myo-Inositol oxygenase from hog kidney. II. Catalytic properties of the homogeneous enzyme. J Biol Chem. Aug. 25, 1981;256(16):8519-24.

Robert-Baudouy et al., [Purification and properties of D-mannonate hydrolase from Escherichia coli K12]. Biochim Biophys Acta. Jun. 6, 1973;309(2):473-85. French.

Robert-Baudouy et al., D-Mannonate and D-altronate dehydratases of Escherichia coli K12. Methods Enzymol. 1982;90 Pt E:288-94.

Robertson et al., Two genes affecting glucarate utilization in Escherichia coli K12. J Gen Microbiol. Apr. 1980;117(2):377-82.

Rodionov et al., Comparative genomics of the KdgR regulon in Erwinia chrysanthemi 3937 and other gamma-proteobacteria. Microbiology. Nov. 2004;150(Pt 11):3571-90.

Singh et al., Calcium glucarate prevents tumor formation in mouse skin. Biomed Environ Sci. Mar. 2003,16(1):9-16.

Thomas et al., Structure/function relationships responsible for the kinetic differences between human type 1 and type 2 3beta-hydroxysteroid dehydrogenase and for the catalysis of the type 1 activity. J Biol Chem. Nov. 8, 2002;277(45):45795-801. Epub Aug. 29, 2002.

(56) References Cited

OTHER PUBLICATIONS

Wagner et al., A new enzymatic method for the determination of free and conjugated glucuronic acid. J. Clin. Chem. Clin. Biochem. May 1976;14(5):225-6.

Wagner et al., Uronic acid dehydrogenase from *Pseudomonas syringae*: Purification and properties. Eur J Biochem. Jan. 1976;61(2):589-96.

Walaszek et al., d-Glucaric acid content of various fruits and vegetables and cholesterol-lowering effects of dietary d-glucarate in the rat. Nutr Res. Apr. 1996;16(4):673-81.

Walaszek, Potential use of D-glucaric acid derivatives in cancer prevention. Cancer Lett. Oct. 8, 1990;54(1-2):1-8.

Werpy et al., Top value added chemicals from Biomass. vol. 1. Results of screening for potential candidates from sugars and synthesis gas. PNNL and NREL. Aug. 2004. 76 pages.

Xing et al., A couple dinuclear iron cluster that is perturbed by substrate binding in myo-inositol oxygenase. Biochemistry. May 2, 2006;45(17):5393-401.

Yebra et al., Identification of a gene cluster enabling *Lactobacillus casei* BL23 to utilize myo-inositol. Appl Environ Microbio. Jun. 2007;73(12):3850-8. Epub Apr. 20, 2007.

Yeh et al., Synthetic biology: lessons from the history of synthetic organic chemistry. Nat Chem Biol. Sep. 2007;3(9):521-5.

Yoon et al. Cloning and characterization of uronate dehydrogenases from two pseudomonads and *Agrobacterium tumefaciens* strain C58. J Bacteriol. Mar. 2009;191(5):1565-73. Epub Dec. 5, 2008.

Yoshida et al., myo-Inositol catabolism in *Bacillus subtilis*. J Biol Chem. Apr. 18, 2008;283(16):10415-24. Epub Feb. 28, 2008.

Zajic, Hexuronic dehydrogenase of *Agrobacterium tumefaciens*. J Bacteriol. Nov. 1959;78:734-5.

GenBank Submission; NCBI, Accession No. AAA34706.1; Dean-Johnson et al.; Nov. 2, 1993.

GenBank Submission; NCBI, Accession No. AF197127.1; Yang et al.; Aug. 30, 2000.

GenBank Submission; NCBI, Accession No. BK006380.1; Yoon et al.; Feb. 19, 2009.

GenBank Submission; NCBI, Accession No. BK006462.1; Yoon et al.; Feb. 19, 2009.

GenBank Submission; NCBI, Accession No. DQ843600.1; Gomez-Jimenez et al.; Dec. 30, 2006.

GenBank Submission; NCBI, Accession No. EU377538.1; Yoon et al.; Jan. 16, 2008.

GenBank Submission; NCBI, Accession No. NP_357458.2; Goodner et al; Nov. 7, 2007.

GenBank Submission; NCBI, Accession No. NP_743331.1; Nelson et al.; Dec. 16, 2002.

Schnoes et al., Annotation error in public databases: misannotation of molecular function in enzyme superfamilies PloS Comput Biol. Dec. 2009;5(12):e1000605. doi: 10.1371/journal.pcbi.1000605. Epub Dec. 11, 2009.

\* cited by examiner

| P. syringae pv. tomato str. DC3000 | | P. putida KT2440 | | A. tumefaciens str. C58 | |
|---|---|---|---|---|---|
| Locus Tag | Product | Locus Tag | Product | Locus Tag | Product |
| PSPTO_1050 | dctQ; TRAP dicarboxylate transporter | PP_1168 | dctQ; TRAP dicarboxylate transporter | Atu3140 | Putative kdgD; 5-dehydro-4-deoxy-D-glucarate dehydratase |
| PSPTO_1051 | dctP; TRAP dicarboxylate transporter | PP_1169 | dctP; TRAP dicarboxylate transporter | Atu3141 | kduD; 2-deoxy-D-gluconate 3-dehydrogenase |
| PSPTO_1052 | Senescence marker protein-30 family protein | PP_1170 | Similar to SMP-30/gluconolactonase/LRE | Atu3142 | kduI; 5-keto-4-deoxyuronate isomerase |
| PSPTO_1053 | udh; uronate dehydrogenase | PP_1171 | udh; uronate dehydrogenase | Atu3143 | udh; uronate dehydrogenase |
| PSPTO_1054 | Outer membrane porin, OprD family | PP_1172 | Hypothetical protein | Atu3144 | L-asparagine operon repressor |
| PSPTO_1055 | Hypothetical protein | PP_1173 | Putative porin protein | Atu3145 | kdgF; pectin degradation protein |

Fig. 11D

```
                        SEQUENCE LISTING

<160> NUMBER OF SEQ ID NOS: 28

<210> SEQ ID NO 1
<211> LENGTH: 828
<212> TYPE: DNA
<213> ORGANISM: Pseudomonas syringae

<400> SEQUENCE: 1
atggcatcgg ctcataccac tcaaactccc ttcaatcgcc tcctgctgac cggtgctgca      60
ggcggcctgg gcaaggtatt gcgcgagaca ttgcgccctt actcacacat tctgcgactc     120
tctgatatcg ccgagatggc gcccgcggtc ggcgaccatg aagaagtgca ggtctgcgat     180
ctggcggaca aagacgccgt acaccgtctg gtcgaaggcg tggacgccat tctgcatttt     240
ggcggcgtgt cggtcgaacg gcctttcgag gaaatcctcg gcgctaatat ctgcggcgtg     300
ttccatatct acgaggccgc ccgccggcat ggcgtgaaac gcgtgatctt cgccagctcc     360
aaccatgtga tcggtttcta caagcagaac gaaaccatcg acgcgcactc cccgcgccgc     420
ccggacagct actatggttt gtccaagtcc tacggcgaag acatggccag cttctacttt     480
gatcgttacg gcatcgaaac cgtcagcatc cgcatcggct catcgttccc tgaaccacag     540
aaccgcagaa tgatgagcac ctggctgagc ttcgatgacc tgacccggtt gctcgagcgc     600
gccctgtaca cgccggacgt cggccacacc gtggtgtatg gcgtgtcgga caacaagacc     660
gtgtggtggg acaaccgctt tgccagcaaa ctggactacg ccctaaaga cagctcggag     720 gtcttccgcg ccaaggtcga cgcccagcca atgccggcg acgacgaccc ggcaatggtt     780
taccagggcg gtgcgtttgt agcgtccgga ccgttcggcg ataaataa               828

<210> SEQ ID NO 2
<211> LENGTH: 275
<212> TYPE: PRT
<213> ORGANISM: Pseudomonas syringae

<400> SEQUENCE: 2

Met Ala Ser Ala His Thr Thr Gln Thr Pro Phe Asn Arg Leu Leu Leu
```

```
1               5                   10                  15
Thr Gly Ala Ala Gly Gly Leu Gly Lys Val Leu Arg Glu Thr Leu Arg
            20                  25                  30
Pro Tyr Ser His Ile Leu Arg Leu Ser Asp Ile Ala Glu Met Ala Pro
            35                  40                  45
Ala Val Gly Asp His Glu Glu Val Gln Val Cys Asp Leu Ala Asp Lys
    50                  55                  60
Asp Ala Val His Arg Leu Val Glu Gly Val Asp Ala Ile Leu His Phe
65                  70                  75                  80
Gly Gly Val Ser Val Glu Arg Pro Phe Glu Glu Ile Leu Gly Ala Asn
                85                  90                  95
Ile Cys Gly Val Phe His Ile Tyr Glu Ala Ala Arg Arg His Gly Val
                100                 105                 110
Lys Arg Val Ile Phe Ala Ser Ser Asn His Val Ile Gly Phe Tyr Lys
            115                 120                 125
Gln Asn Glu Thr Ile Asp Ala His Ser Pro Arg Arg Pro Asp Ser Tyr
    130                 135                 140
Tyr Gly Leu Ser Lys Ser Tyr Gly Glu Asp Met Ala Ser Phe Tyr Phe
145                 150                 155                 160
Asp Arg Tyr Gly Ile Glu Thr Val Ser Ile Arg Ile Gly Ser Ser Phe
                165                 170                 175
Pro Glu Pro Gln Asn Arg Arg Met Met Ser Thr Trp Leu Ser Phe Asp
            180                 185                 190
Asp Leu Thr Arg Leu Leu Glu Arg Ala Leu Tyr Thr Pro Asp Val Gly
            195                 200                 205
His Thr Val Val Tyr Gly Val Ser Asp Asn Lys Thr Val Trp Trp Asp
    210                 215                 220
Asn Arg Phe Ala Ser Lys Leu Asp Tyr Ala Pro Lys Asp Ser Ser Glu
225                 230                 235                 240
Val Phe Arg Ala Lys Val Asp Ala Gln Pro Met Pro Ala Asp Asp
                245                 250                 255
Pro Ala Met Val Tyr Gln Gly Gly Ala Phe Val Ala Ser Gly Pro Phe
            260                 265                 270
Gly Asp Lys
        275
```

<210> SEQ ID NO 3
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 3
gaattcatga cagaagataa tattgctc                                    28

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
aagcttctac aacaatctct cttcg                                       25

<210> SEQ ID NO 5

```
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 5
aggaggtaat aaat                                                   14

<210> SEQ ID NO 6
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 6
cgaattcagg aggtacaacc atgcctgttt cag                              33

<210> SEQ ID NO 7
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 7
cgtcgactta tcgcgcatcg gccagcagtt g                                31

<210> SEQ ID NO 8
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 8
cgaattcagg aggattgaat catgagtc                                    28

<210> SEQ ID NO 9
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 9
cgtcgactta aagatccagc agccagc                                     27

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
gccatggcat cggctcatac cac                                         23

<210> SEQ ID NO 11
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 11
```
cgagctctta tttatcgccg aacggtcc                                           28

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 12
ctagaattca tgaaacggct tcttgttacc                                         30

<210> SEQ ID NO 13
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 13
ctagagctct tagctctgtt tgaagatcgg gttg                                    34

<210> SEQ ID NO 14
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 14
gtcgaattca tgaccactac cccttcaat c                                        31

<210> SEQ ID NO 15
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 15
ctagagctcc gtggggttag ttgaacgggc                                         30

<210> SEQ ID NO 16
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 16
ctagaattca tggcatcggc tcataccact c                                       31

<210> SEQ ID NO 17
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 17
tcagagctcg aaacggcttc ttgttaccgg tgc                                     33

<210> SEQ ID NO 18
<211> LENGTH: 34
<212> TYPE: DNA

```
<213> ORGANISM: Artificial Sequence
<220> FEATURE:
<223> OTHER INFORMATION: synthetic oligonucleotide

<400> SEQUENCE: 18
ctgaagcttg ctctgtttga agatcgggtt gtcg                               34

<210> SEQ ID NO 19
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 19
tcagagctcg accactaccc ccttcaatcg cc                                 32

<210> SEQ ID NO 20
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 20
ctgaagcttg ttgaacgggc cggccacggc g                                  31

<210> SEQ ID NO 21
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 21
tcagagctcg gcatcggctc ataccactca aactcc                             36

<210> SEQ ID NO 22
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 22
ctgaagcttt ttatcgccga acggtccgga cgc                                33

<210> SEQ ID NO 23
<211> LENGTH: 798
<212> TYPE: DNA
<213> ORGANISM: Agrobacterium tumefaciens

<400> SEQUENCE: 23
atgaaacggc ttcttgttac cggtgcggcg ggccagcttg ccgcgtcat gcgcgagcgt     60 ctcgcaccga tggcggagat actgcgcctt gccgatctct ccccgctcga cccggcaggg   120
ccgaacgaag aatgcgtgca atgcgacctt gccgatgcca atgccgtgaa tgccatggtc   180
gccggttgcg acgtattgt tcatctcggc ggcatctcgg tggagaagcc cttcgaacaa   240
atccttcagg gcaatatcat cgggctttat aatctctacg aggccgcccg cgcccatgga   300
cagccacgca tcgtctttgc cagctccaac cacacgatcg gctattatcc gcagaccgaa   360
cggctcggtc cggatgttcc ggcgcggccg acggtctttt acggcgtctc caaatgtttc   420
ggcgaaaacc tcgcccgcat gtatttcgat aaattcgggc aggagacggc gctggtgcgc   480
```

-continued

```
atcggctcct gtacgccgga acccaacaat taccgcatgc tgtccacctg gttttcgcac      540
gatgatttcg tgtcgctgat cgaggcggtg tttcgcgcgc cggtgctcgg ctgcccggtc      600 gtctggggg catcggccaa tgatgcgggc tggtgggaca attcgcatct tggctttctg      660
ggctggaaac cgaaggataa tgccgaggcc ttccggcggc atataaccga dacgacaccg      720
ccaccggacc cgaatgacgc gttggtgcgg ttccagggcg gtacgtttgt cgacaacccg      780
atcttcaaac agagctga                                                   798
```

<210> SEQ ID NO 24
<211> LENGTH: 265
<212> TYPE: PRT
<213> ORGANISM: Agrobacterium tumefaciens

<400> SEQUENCE: 24

```
Met Lys Arg Leu Leu Val Thr Gly Ala Ala Gly Gln Leu Gly Arg Val
1               5                   10                  15

Met Arg Glu Arg Leu Ala Pro Met Ala Glu Ile Leu Arg Leu Ala Asp
            20                  25                  30

Leu Ser Pro Leu Asp Pro Ala Gly Pro Asn Glu Glu Cys Val Gln Cys
        35                  40                  45

Asp Leu Ala Asp Ala Asn Ala Val Asn Ala Met Val Ala Gly Cys Asp
    50                  55                  60

Gly Ile Val His Leu Gly Ile Ser Val Glu Lys Pro Phe Glu Gln
65                  70                  75                  80

Ile Leu Gln Gly Asn Ile Ile Gly Leu Tyr Asn Leu Tyr Glu Ala Ala
                85                  90                  95

Arg Ala His Gly Gln Pro Arg Ile Val Phe Ala Ser Ser Asn His Thr
            100                 105                 110

Ile Gly Tyr Tyr Pro Gln Thr Glu Arg Leu Gly Pro Asp Val Pro Ala
        115                 120                 125

Arg Pro Asp Gly Leu Tyr Gly Val Ser Lys Cys Phe Gly Glu Asn Leu
    130                 135                 140

Ala Arg Met Tyr Phe Asp Lys Phe Gly Gln Glu Thr Ala Leu Val Arg
145                 150                 155                 160

Ile Gly Ser Cys Thr Pro Glu Pro Asn Asn Tyr Arg Met Leu Ser Thr
                165                 170                 175

Trp Phe Ser His Asp Asp Phe Val Ser Leu Ile Glu Ala Val Phe Arg
            180                 185                 190

Ala Pro Val Leu Gly Cys Pro Val Val Trp Gly Ala Ser Ala Asn Asp
        195                 200                 205

Ala Gly Trp Trp Asp Asn Ser His Leu Gly Phe Leu Gly Trp Lys Pro
    210                 215                 220

Lys Asp Asn Ala Glu Ala Phe Arg Arg His Ile Thr Glu Thr Thr Pro
225                 230                 235                 240

Pro Pro Asp Pro Asn Asp Ala Leu Val Arg Phe Gln Gly Gly Thr Phe
                245                 250                 255

Val Asp Asn Pro Ile Phe Lys Gln Ser
            260                 265
```

<210> SEQ ID NO 25
<211> LENGTH: 807
<212> TYPE: DNA
<213> ORGANISM: Pseudomonas putida

<400> SEQUENCE: 25

```
atgaccacta ccccttcaa tcgcctgctg ctcaccggag ccgcaggcgg cctgggcaag    60
gtccttcgcg aacgcctgaa aggctacgcc gaggtcctgc gcctgtctga catcagcccc   120
atggccccgg ccgcgggccc gcatgaagaa gtcattacct gtgacctggc cgacaaggct   180
gcggtgcata ccctggtcga gggcgtagac gccatcatcc actttggcgg ggtttctacc   240
gaacacgcct tcgaagagat tctcggcccc aatatctgcg gcgtgttcca cgtgtacgag   300
gcggcgcgca agcacggggt caagcgcatc atcttcgcca gctccaacca caccatcggt   360
ttctatcgcc aggatgagcg catcgacgct cacgcgccgc gccggcccga cagctattac   420
gggctgtcca gtgctacgg cgaagatgtg ccagcttct actttgaccg ctacggcatc   480
gagaccgtca gcattcgcat cggctcgtcg ttcccgcagc cacagaacct gcgcatgctc   540
tgcacctggc tcagttacga cgacctggtg cagttgatcg aacgcgggct gttcaccccc   600
ggggttggcc acaccatcgt ctacggcgcc tccgacaatc gcaccgtgtg gtgggacaac   660
cgccatgccg cgcacctggg ctatgtaccc aaggacagct ccgaaacctt ccgcgcagcc   720
gtggaggccc aaccggcacc cgccgccgat gacccgagca tggtctacca gggcggcgct   780
ttcgccgtgg ccggcccgtt caactga                                      807
```

<210> SEQ ID NO 26  
<211> LENGTH: 268  
<212> TYPE: PRT  
<213> ORGANISM: Pseudomonas putida

<400> SEQUENCE: 26

```
Met Thr Thr Thr Pro Phe Asn Arg Leu Leu Leu Thr Gly Ala Ala Gly
  1               5                  10                  15

Gly Leu Gly Lys Val Leu Arg Glu Arg Leu Lys Gly Tyr Ala Glu Val
             20                  25                  30

Leu Arg Leu Ser Asp Ile Ser Pro Met Ala Pro Ala Ala Gly Pro His
         35                  40                  45

Glu Glu Val Ile Thr Cys Asp Leu Ala Asp Lys Ala Ala Val His Thr
     50                  55                  60

Leu Val Glu Gly Val Asp Ala Ile Ile His Phe Gly Gly Val Ser Thr
 65                  70                  75                  80

Glu His Ala Phe Glu Glu Ile Leu Gly Pro Asn Ile Cys Gly Val Phe
                 85                  90                  95

His Val Tyr Glu Ala Ala Arg Lys His Gly Val Lys Arg Ile Ile Phe
            100                 105                 110

Ala Ser Ser Asn His Thr Ile Gly Phe Tyr Arg Gln Asp Glu Arg Ile
        115                 120                 125

Asp Ala His Ala Pro Arg Arg Pro Asp Ser Tyr Tyr Gly Leu Ser Lys
    130                 135                 140

Cys Tyr Gly Glu Asp Val Ala Ser Phe Tyr Phe Asp Arg Tyr Gly Ile
145                 150                 155                 160

Glu Thr Val Ser Ile Arg Ile Gly Ser Ser Phe Pro Gln Pro Gln Asn
                165                 170                 175

Leu Arg Met Leu Cys Thr Trp Leu Ser Tyr Asp Asp Leu Val Gln Leu
            180                 185                 190

Ile Glu Arg Gly Leu Phe Thr Pro Gly Val Gly His Thr Ile Val Tyr
        195                 200                 205

Gly Ala Ser Asp Asn Arg Thr Val Trp Trp Asp Asn Arg His Ala Ala
    210                 215                 220
```

His Leu Gly Tyr Val Pro Lys Asp Ser Ser Glu Thr Phe Arg Ala Ala
225                 230                 235                 240

Val Glu Ala Gln Pro Ala Pro Ala Ala Asp Asp Pro Ser Met Val Tyr
            245                 250                 255

Gln Gly Gly Ala Phe Ala Val Ala Gly Pro Phe Asn
        260                 265

<210> SEQ ID NO 27
<211> LENGTH: 858
<212> TYPE: DNA
<213> ORGANISM: Artificial Sequence
<220> FEATURE:
<223> OTHER INFORMATION: Synthetic Polynucleotide

<400> SEQUENCE: 27
atgaaagttg atgttggtcc tgatccgtct ctggtttatc gtccagacgt ggatccggag      60
atggcaaaga gcaaagactc tttccgtaac tacacttctg gtccgctgct ggatcgcgtt     120
ttcacgacct acaaactgat gcacacccat cagaccgttg atttcgtgag ccgcaagcgc     180
atccagtatg gttctttctc ttacaaaaag atgaccatta tggaggctgt tggtatgctg     240
gatgacctgg ttgacgaaag cgaccctgac gttgacttcc taactctttt ccatgcattt     300
cagaccgccg aaggtattcg taaagctcat cctgataaag attggttcca cctggtcggt     360
ctgctgcacg acctgggtaa gatcatggcg ctgtggggcg aaccacaatg gcggtagtg      420
ggcgatactt tccggtgggg ctgccgccca caggcatccg tggtcttctg cgactctacc     480
ttccaggata acccggatct gcaggatccg cgctattcca ccgaactggg catgtaccag     540
ccgcattgcg gcctggagaa cgttctgatg tcttggggtc acgacgagta cctgtatcag     600
atgatgaaat caacaaaatt ctccctgccg tccgaggcat tttacatgat ccgttttcac     660
tccttctacc gtggcatac cggtggcgat tatcgtcagc tgtgctctca gcaggatctg     720
gatatgctgc cgtgggttca ggagttcaat aaattcgacc tgtataccaa atgccctgac     780
ctgccagatg ttgaatccct cgcccatac taccaaggcc tgattgacaa atactgcccg     840
ggcacccctgt cctggtaa                                                   858

<210> SEQ ID NO 28
<211> LENGTH: 858
<212> TYPE: DNA
<213> ORGANISM: Mus musculus

<400> SEQUENCE: 28
atgaaggtcg atgtgggccc agacccttcc ctggtctatc gacccgatgt ggacccagag      60
atggccaaaa gcaaggacag cttccgaaac tatacttcag gcccgctgct ggatcgtgtc     120
tttaccacat acaagctcat gcacactcac cagactgtgg acttcgtcag caggaagcgc     180
atccagtatg gaagcttctc ttacaagaag atgaccatca tggaggctgt gggcatgctg     240
gatgatctgg tggacgaatc tgacccagac gtagatttcc ccaactcctt ccacgcgttc     300
cagaccgcgg agggcatccg gaaagcccac ccggacaagg actggttcca cctggtcgga     360
cttttgcacg atctggggaa aattatggct ctgtgggggg aacctcagtg gctgttgtt      420
ggagacacgt tccccgtggg ctgccgtccc caggcctctg tggtgttctg tgactctact     480
ttccaggaca atcctgacct ccaggatcct cgatacagca cagaactcgg catgtaccag     540
cctcactgtg gactagagaa cgtccttatg tcctggggcc atgatgagta cctataccag     600
atgatgaagt caacaagtt ctccctgcct tcagaggcct ctacatgat ccgattccac      660

| | | | | | |
|---|---|---|---|---|---|
| tccttctatc | cgtggcacac | cggcggtgac | taccggcagc | tgtgcagcca | gcaggacctg | 720 |
| gatatgctgc | cctgggtgca | agagttcaac | aagtttgatc | tctacacgaa | gtgccctgac | 780 |
| ctaccggatg | tggagagcct | gcggccctac | tatcaagggc | tgattgacaa | gtactgcccg | 840 |
| ggcaccctga | gctggtga | | | | | 858 |

CELLULAR PRODUCTION OF GLUCARIC ACID THROUGH RECOMBINANT EXPRESSION OF URONATE DEHYDROGENASE AND MYO-INOSITOL OXYGENASE

RELATED APPLICATIONS

This application is a national stage filing under 35 U.S.C. §371 of international application PCT/US2009/002111, filed Apr. 3, 2009, which was published under PCT Article 21(2) in English, and claims the benefit under 35 U.S.C. §119(e) of U.S. Provisional Application Serial No. 61/042,502, entitled "Microbial Production of Glucaric Acid," filed on Apr. 4, 2008, the disclosures of which are herein incorporated by reference in their entireties.

GOVERNMENT INTEREST

This work was funded in part by the Office of Naval Research under grant number N000140510656. The government has certain rights in this invention.

FIELD OF THE INVENTION

The invention relates to the production of glucuronic and glucaric acid through recombinant gene expression.

BACKGROUND OF THE INVENTION

Metabolic engineering, encompassing application of recombinant DNA technology, has shown its potential to optimize cellular functions for many purposes: recombinant protein production, pathway engineering for productivity enhancement, and novel pathway design for new product generation. Defined as a sequence of conversions that is not found in host species, a novel pathway has been designed and constructed in *E. coli* for the production of 1,3-propanediol (C. E. Nakamura and G. M. Whited (2003). *Curr. Opin. Biotechnol.* 14: 454-459), amorphadiene (Nature Biotech, 21, pp 796-802), and 1,2,4-butanetriol (JACS, 125, pp 12998-12999). In these approaches, each step was designed based on enzyme availability, the recruited enzyme activities from various organisms were identified, and the novel pathways were constructed in *E. coli* by assembling these enzymatic steps. The basic idea behind these examples is to consider proteins including enzymes as interchangeable parts, and the term "synthetic biology" has been used to describe this concept (Nature 421, p 118; Nature Chemical Biology, 3, pp 521-525).

D-glucaric acid is found in fruits, vegetables, and mammals and has been studied for cholesterol reduction (Z. Walaszek, et al. (1996). *Nutr. Res.* 16: 673-681) and cancer chemotherapy (J. Singh and K. P. Gupta (2003). *Biomed. Environ. Sci.* 16: 9-16). In a recent report (T. Werpy and G. Petersen (2004). "Top Value Added Chemicals From Biomass," Vol. I, PNNL and NREL), D-glucaric acid was identified as a "Top Value Added Chemicals From Biomass" and as a promising starting material for producing new nylons and hyperbranched polyesters. D-glucaric acid, a highly functionalized compound with four chiral carbons, is currently produced by chemical oxidation of D-glucose, a nonselective and expensive process using nitric acid as the oxidant (T. Werpy and G. Petersen (2004). "Top Value Added Chemicals From Biomass," Vol. I, PNNL and NREL). New catalytic processes using enzymes may lead to higher yield and selectivity. The biological approach for producing glucaric acid could be made by mimicking the existing D-glucuronic acid pathway in mammals. However, this is an inefficient pathway, which consists of more than ten conversion steps, starting with D-glucose.

SUMMARY OF THE INVENTION

Described herein is the cloning and characterization of the first udh genes encoding uronate dehydrogenase. Further described herein is the construction of a novel pathway for the production of either D-glucuronic or D-glucaric acid in a cell such as an *E. coli* cell, by combining "biological parts" from disparate organisms. A first enzyme, myo-inositol 1-phosphate synthase (Ino1/MIPS), produces myo-inositol from glucose, through glucose-6-phospate as an intermediate (Dean-Johnson and Henry 1989). A second enzyme, myo-inositol oxygenase (MIOX), converts myo-inositol to glucuronic acid. Co-expression of these two enzymes in a cell such as an *E. coli* cell enables the production of glucuronic acid from glucose. Uronate dehydrogenase can convert glucuronic acid to glucaric acid (Bateman, Kosuge et al. 1970; Wagner and Hollman 1976). As described herein, expression of this third gene with INO1 and MIOX enables the production of glucaric acid from glucose. Surprisingly, recombinant expression of uronate dehydrogenase increased the flux of the pathway significantly such that high quantities of glucaric acid could be obtained.

The invention provides a cell that recombinantly expresses a gene encoding uronate dehydrogenase and recombinantly expresses a gene encoding myo-inositol oxygenase. In some embodiments the gene encoding uronate dehydrogenase is a bacterial gene, such as a *Pseudomonas syringae* gene or an *Agrobacterium tumefaciens* gene. In some embodiments the gene encoding myo-inositol oxygenase is a mammalian gene such as a mouse gene. In some embodiments the cell also recombinantly expresses a gene encoding myo-inositol 1-phosphate synthase. The gene encoding myo-inositol 1-phosphate synthase in some embodiments may be a fungal gene or a yeast gene such as a *Saccharomyces cerevisiae* gene.

The cell that is recombinantly expressing the enzymes described above can be a prokaryotic or a eukaryotic cell. In some embodiments the cell is a bacterial cell such as an *E. coli* cell. In some embodiments the genes encoding myo-inositol oxygenase and/or myo-inositol 1-phosphate synthase have been modified by codon optimization for expression in bacteria. In some embodiments the cell is a fungal cell, a yeast cell, an insect cell, a plant cell or a mammalian cell.

The genes encoding uronate dehydrogenase, myo-inositol oxygenase and/or myo-inositol 1-phosphate synthase can be expressed from plasmids or can be integrated into the genome of the cell. In some embodiments the production of glucaric acid is increased by protein engineering of the uronate dehydrogenase, myo-inositol oxygenase and/or myo-inositol 1-phosphate synthase enzymes in the cell, or by mutating a component of the glucaric acid metabolism pathway in the cell. The invention includes in some embodiments a genetically modified microorganism that comprises one or more recombinant nucleic acid molecules encoding uronate dehydrogenase, myo-inositol oxygenase and myo-inositol 1-phosphate synthase.

The invention also provides methods for producing glucuronic acid and glucaric acid comprising culturing a cell associated with the invention, to produce glucuronic acid or glucaric acid and recovering the glucuronic or glucaric acid from the cells. In some embodiments the method for producing glucuronic or glucaric acid comprises genetically modifying a cell to recombinantly express at least one of: uronate dehydrogenase, myo-inositol oxygenase and myo-inositol 1-phosphate synthase, culturing a population of said cells, and collecting glucaric acid from the population of cells that have been genetically modified to produce glucaric acid.

In some embodiments the cell recombinantly expresses myo-inositol oxygenase and produces glucuronic acid. In some embodiments the cell recombinantly expresses myo-inositol oxygenase and myo-inositol 1-phosphate synthase and produces glucuronic acid. In some embodiments the cell recombinantly expresses myo-inositol oxygenase and uronate dehydrogenase and produces glucaric acid. In some embodiments the cell recombinantly expresses myo-inositol oxygenase, myo-inositol 1-phosphate synthase and uronate dehydrogenase and produces glucaric acid.

In some embodiments the recombinantly expressed gene encoding uronate dehydrogenase is a bacterial gene such as a *Pseudomonas syringae* gene or an *Agrobacterium tumefaciens* gene. In some embodiments the recombinantly expressed gene encoding myo-inositol oxygenase is a mammalian gene such as a mouse gene. In some embodiments the recombinantly expressed gene encoding myo-inositol 1-phosphate synthase is a fungal gene or a yeast gene such as a *Saccharomyces cerevisiae* gene. In some embodiments the cell that is recombinantly expressing the enzymes described above is a prokaryotic cell. In certain embodiments the cell is a bacterial cell such an *E. coli* cell. The genes encoding myo-inositol oxygenase and/or myo-inositol 1-phosphate synthase may be modified by codon optimization for expression in bacteria.

In some embodiments the cell that is recombinantly expressing the enzymes described above is a eukaryotic cell. In certain embodiments the cell is a fungal cell, a yeast cell, an insect cell, a plant cell or a mammalian cell. The genes encoding uronate dehydrogenase, myo-inositol oxygenase and/or myo-inositol 1-phosphate synthase can be expressed on plasmids or integrated into the genome of the cell. The production of glucaric acid can be increased by protein engineering of the uronate dehydrogenase, myo-inositol oxygenase and/or myo-inositol 1-phosphate synthase enzymes in the cell, or by mutating a component of the glucaric acid metabolism pathway in the cell.

The invention also provides glucaric acid that is produced by the cells and methods described above. In some embodiments the glucaric acid is produced by a cell culture wherein the cells within the cell culture have been genetically modified to recombinantly express at least one of: uronate dehydrogenase, myo-inositol oxygenase and myo-inositol 1-phosphate synthase. In some embodiments the gene encoding uronate dehydrogenase is a bacterial gene such as a *Pseudomonas syringae* gene or an *Agrobacterium tumefaciens* gene.

In some embodiments the gene encoding myo-inositol oxygenase is a mammalian gene such as a mouse gene. In some embodiments the gene encoding myo-inositol 1-phosphate synthase is a fungal gene or a yeast gene such as a *Saccharomyces cerevisiae* gene.

In some embodiments the glucaric acid is produced from a prokaryotic cell. In some embodiments the prokaryotic cell is a bacterial cell such as an *E. coli* cell. The genes encoding for myo-inositol oxygenase and/or myo-inositol 1-phosphate synthase are in some embodiments modified by codon optimization for expression in bacteria. The glucaric acid can also be produced by a eukaryotic cell. In certain embodiments the cell is a fungal, a yeast cell, an insect cell, a plant cell or a mammalian cell.

For the production of glucaric acid, the genes encoding uronate dehydrogenase, myo-inositol oxygenase and/or myo-inositol 1-phosphate synthase can be expressed on plasmids or integrated into the genome of the cell. In some embodiments the production of glucaric acid is increased by protein engineering of the uronate dehydrogenase, myo-inositol oxygenase and/or myo-inositol 1-phosphate synthase enzymes in the cell, or by mutating a component of the glucaric acid metabolism pathway in the cell.

The invention also includes isolated nucleic acid molecules including: (a) an isolated nucleic acid molecule comprising SEQ ID NO:1, SEQ ID NO:23, or SEQ ID NO:25; (b) an isolated nucleic acid molecule encoding an amino acid sequence comprising the sequence of SEQ ID NO:2, SEQ ID NO: 24 or SEQ ID NO:26; (c) an isolated nucleic acid molecule that is a reverse complement of the full-length sequence of (a) or (b); and (d) an isolated nucleic acid molecule that has at least 95% nucleotide identity to any one of (a)-(c). Also encompassed by the invention is a recombinant expression vector comprising the nucleic acid molecules discussed above, operably linked to a transcription regulatory element. The invention also includes isolated uronate dehydrogenase polypeptides encoded by the nucleic acid molecules described herein. In some embodiments the isolated uronate dehydrogenase polypeptide comprising at least 95% amino acid identity to SEQ ID NO:2, SEQ ID NO:24 or SEQ ID NO:26.

The invention includes cells that contain the recombinant expression vectors described herein. In certain embodiments the cell is a bacterial cell, a fungal cell, a yeast cell, a plant cell, an insect cell or an animal cell. The cell that recombinantly expresses the uronate dehydrogenase gene can be used to produce uronate dehydrogenase protein by culturing the cell under conditions that permit expression of the polypeptide and recovering the polypeptide from the culture medium or the cell.

The invention also includes isolated antibodies which selectively bind to the uronate dehydrogenase polypeptides described herein. In some embodiments the antibodies selectively bind to a polypeptide comprising at least 95% amino acid identity to SEQ ID NO:2. In some embodiments the antibodies bind to a polypeptide encoded by a nucleic acid comprising at least 95% nucleotide identity with SEQ ID NO:1. The antibody can be a polyclonal antibody, a monoclonal antibody, a chimeric antibody, a humanized antibody, or an antigen-binding fragment thereof.

BRIEF DESCRIPTION OF THE DRAWINGS

FIG. 4 is a DNA sequence alignment of the mouse MIOX gene (SEQ ID NO:28) and its synthesized version with codon optimization for expression in E. coli (SEQ ID NO:27). DNA sequence alignment was carried out using Vector NTI software (Invitrogen, Carlsbad, CA).

FIG. 8 depicts an LC-MS chromatogram of glucarate.

FIG. 10 is a graph depicting the effect of pH and temperature on activities of purified Udhs from A. tumefaciens, P. putida, and P. syringae udh.

FIG. 11 presents a schematic showing loci of udh genes on chromosomes and a table depicting adjacent genes. FIG. 11d is a table showing the identities of adjacent genes. These loci and identities are referenced to the genome sequences of NC_004578 (P. syringae pv. tomato str. DC3000), NC_002947 (P. putida KT2440) and NC 003063 (A. tumefaciens str. C58).

FIG. 12 presents a sequence alignment and phylogenetic analysis.

DETAILED DESCRIPTION OF THE INVENTION

Figure 1:
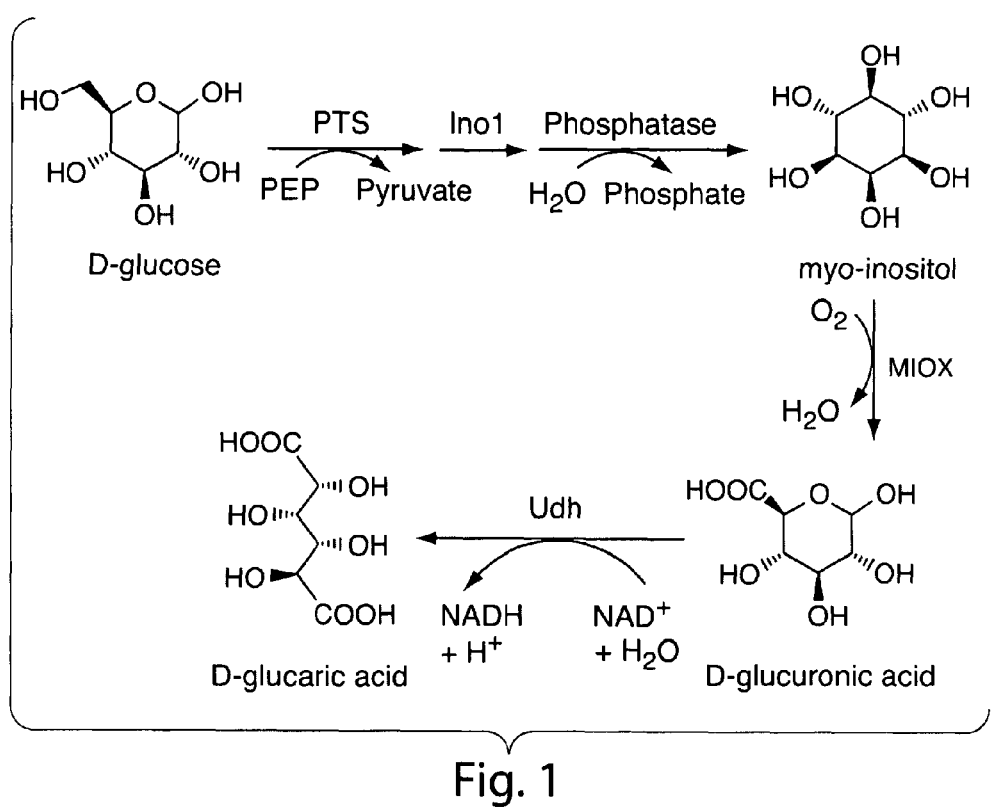
FIG. 1 is a schematic showing the designed pathway for the production of glucaric acid in *E. coli*. PTS=phosphoenolpyruvate-dependent phosphotransferase system; Ino1 (MIPS)=myo-inositol 1-phosphate synthase from *Saccharomyces cerevisiae*; Phosphatase=SuhB, endogenous *E. coli* enzyme (Matsuhisa et al. *J. Bacteriol.* (1995) 177:200-205); MIOX=mouse version of myo-inositol oxygenase with codon optimization; Udh=uronate dehydrogenase from *Pseudomonas syringae*; PEP=phosphoenolpyruvate.

Aspects of the invention relate to methods and compositions for the production of glucuronic and glucaric acid through recombinant gene expression in cells. Described herein is the cloning of a gene encoding uronate dehydrogenase, an enzyme that converts glucuronic acid to glucaric acid. Novel pathways are described that have been designed and implemented to produce glucuronic and glucaric acid from glucose through recombinant expression of uronate dehydrogenase in combination with myo-inositol 1-phosphate synthase and myo-inositol oxygenase. This novel pathway represents an unexpectedly efficient new system for producing glucaric acid, a molecule with widespread applications ranging from production of nylons and polyester to cancer therapy.

The novel pathways described herein for the production of glucuronic and glucaric acid in cells involve several enzymatic components. A first enzyme, myo-inositol 1-phosphate synthase (Ino1/MIPS), encoded by the INO1 gene of Saccharomyces cerevisiae, produces myo-inositol from glucose, through glucose-6-phospate as an intermediate (Dean-Johnson and Henry 1989). The Saccharomyces cerevisiae sequence, for example, has GenBank accession number NC_001142 (GeneID: 853288). In yeast, myo-inositol is a constituent of membrane phospholipids, and its derivatives are important for cell signaling. The MIPS substrate, glucose-6-phosphate, is present in E. coli as the result of glucose transport by the PTS system (Postma, Lengeler et al. 1993). A second enzyme, myo-inositol oxygenase (MIOX), converts myo-inositol to glucuronic acid. This enzyme is present primarily in mammalian sources and represents the first step of myo-inositol catabolism (Charalampous and Lyras 1957). The mouse sequence, for example, has GenBank accession number NC_000081 (GeneID: 56727). Co-expression of these two enzymes in a cell such as an E. coli enables the production of glucuronic acid from glucose.

The third step in the novel pathway for the production of glucaric acid is the conversion of glucuronic acid to glucaric acid, a step that can be performed by uronate dehydrogenase (Bateman, Kosuge et al. 1970; Wagner and Hollman 1976). As described in Example 2, genes encoding uronate dehydrogenase were cloned and characterized in order to construct this pathway. As presented in Example 2, uronate dehydrogenase was cloned from Pseudomonas syringae pv. tomato DC300, Pseudomonas putida KT2440 and Agrobacterium

*tumefaciens* str. C58. The udh gene sequence from *P. syringae* has been deposited with GenBank, Accession Number EU377538. The DNA and protein sequences of *Pseudomonas syringae* pv. tomato DC300A udh are provided in SEQ ID NOs:1 and 2 respectively. The corresponding genes from *A. tumefaciens* and *P. putida* were deposited with Accession Numbers BK006462 (DNA: SEQ ID NO:23; protein: SEQ ID NO:24) and BK006380 (DNA: SEQ ID NO:25; protein: SEQ ID NO:26), respectively. Cloning of uronate dehydrogenase allows identification of uronate dehydrogenase proteins in various species, using standard methods of homology searching known in the art, such as through a BLAST search.

As described herein, coexpression of myo-inositol 1-phosphate synthase and myo-inositol oxygenase in a cell leads to production of glucuronic acid from glucose. When the cell expressing these enzymes further expresses uronate dehydrogenase, this leads to an unexpectedly efficient level of production of glucaric acid from glucose via a three-step pathway consisting of: 1) production of myo-inositol from glucose, 2) conversion of myo-inositol to glucuronic acid, and 3) conversion of glucuronic acid to glucaric acid. Also encompassed by the invention is a two-step pathway that bypasses the first step described above, and consists of steps 2 and 3. In this particular embodiment a cell that could generate glucose would be used, precluding the need to supply glucose to the growth medium of the cell. In some embodiments such a cell is provided with a glucose polymer such as corn starch.

Aspects of the invention relate to cells that recombinantly express at least one of: myo-inositol 1-phosphate synthase, myo-inositol oxygenase and uronate dehydrogenase. The invention encompasses any type of cell including prokaryotic and eukaryotic cells, in some embodiments the cell is a bacterial cell such as an *E. coli* cell. In other embodiments the cell is a fungal cell or yeast cell such as a *S. cerevisiae* cell. In other embodiments the cell is a mammalian cell such as a mouse cell. It should be appreciated that some cells may express at least one of the enzymes associated with the invention endogenously. In some embodiments a cell will not express any of the enzymes endogenously and will express one, two or three of the enzymes recombinantly. In other embodiments a cell will express one of the enzymes endogenously and the other one or two enzymes recombinantly. In other enzymes a cell will express two of the enzymes endogenously and the other one or two enzymes recombinantly.

In some embodiments a cell will express one or more of the genes endogenously and will also express the same one or more genes recombinantly.

In some embodiments genes encoding for myo-inositol 1-phosphate synthase, myo-inositol oxygenase and uronate dehydrogenase are expressed in recombinant expression vectors. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of a novel pathway for production of glucaric acid is demonstrated in the Examples section using *E. coli*. The novel glucaric acid production pathway can also be expressed in other bacterial cells, archael cells, fungi, mammalian cells, plant cells, etc.

In some embodiments two or more of the nucleic acids of the invention may be cloned into the same expression vector or plasmid. As discussed in the Example section, in some embodiments, the INO1 gene and the MIOX gene are cloned into the same plasmid such as the pRSFD plasmid.

A nucleic acid molecule or nucleic acid molecules that encodes any of the enzymes for producing glucaric acid can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule(s) encoding the enzymes for producing glucaric acid also may be accomplished by integrating the nucleic acid molecule into the genome. Nucleic acid molecule(s) can be integrated into a cell's genomic DNA using standard techniques well known in the art.

In some embodiments the enzymes associated with the invention are expressed recombinantly in a bacterial cell. Bacterial cells according to the invention can be cultured in media of any type (rich or minimal) and composition. Example 1 presents an embodiment in which rich media (LB media, BD Biosciences; San Jose, Calif.), that was supplemented with glucose and induced with IPTG, was found to be optimal. As would be understood by one of ordinary skill in the art, routine optimization would allow for use of other types of media including minimal media such as M9 minimal medium. The selected medium can be supplemented with various additional components. Similarly, other aspects of the medium and growth conditions may be optimized through routine experimentation. For example, pH and temperature are non-limiting examples of factors which can be optimized. According to aspects of the invention, the liquid cultures used to grow cells can be housed in any of the culture vessels known and used in the art.

Aspects of the invention include strategies to optimize glucaric acid production from a cell. Optimized production of glucaric acid refers to producing a higher amount of glucaric acid following pursuit of an optimization strategy than would be achieved in the absence of such a strategy. One strategy is to optimize expression levels of myo-inositol 1-phosphate synthase, myo-inositol oxygenase and/or uronate dehydrogenase through selection of appropriate promoters and ribosome binding sites. In some embodiments this may include the selection and use of high-copy number plasmids, or low or medium-copy number plasmids. The step of transcription termination can also be targeted for regulation of gene expression, through the introduction or elimination of structures such as stem-loops.

In some embodiments it may be advantageous to use a cell that has been previously optimized for production of glucaric acid. For example it may be optimal to mutate one or more components of the glucaric acid metabolism pathway in the cell, prior to the production of glucaric acid, so that the cell does not consume the product being produced. In some embodiments, screening for mutations that lead to enhanced production of glucaric acid may be conducted through a random mutagenesis screen, or through screening of known mutations. In some embodiments shotgun cloning of genomic fragments could be used to identify genomic regions that lead to an increase in glucaric acid production, through screening cells or organisms that have these fragments for increased glucaric acid production. In some cases one or more mutations may be combined in the same cell or organism.

Optimization of protein expression may also require in some embodiments that the genes encoding for the enzymes associated with the invention be modified before being introduced into a cell such as through codon optimization for expression in a bacterial cell. Codon usages for a variety of organisms can be accessed in the Codon Usage Database interne site. For example the invention encompasses a mouse MIOX gene that has been synthesized with codon optimization for expression in *E. coli*.

In some embodiments protein engineering can be used to optimize expression or activity of one or more of the enzymes associated with the invention. In certain embodiments a protein engineering approach could include determining the three-dimensional (3D) structure of an enzyme or constructing a 3D homology model for the enzyme based on the structure of a related protein. Based on 3D models, mutations in an enzyme can be constructed and incorporated into a cell or organism, which could then be screened for an increased production of glucaric acid. In some embodiments glucaric acid production in a cell could be increased through manipulation of enzymes that act in the same pathway as the enzymes associated with the invention. For example in some embodiments it may be advantageous to increase expression of an enzyme or other factor that acts upstream of one of the enzymes associated with the invention. This could be achieved by over-expressing the upstream factor using any standard method.

The invention thus involves in one aspect uronate dehydrogenase polypeptides, genes encoding those polypeptides, functional modifications and variants of the foregoing, as well as uses relating thereto. Homologs and alleles of the uronate dehydrogenase nucleic acids of the invention can be identified by conventional techniques. Also encompassed by the invention are nucleic acids that hybridize under stringent conditions to the uronate dehydrogenase nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of uronate dehydrogenase nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 90% amino acid identity to the sequences of uronate dehydrogenase nucleic acid and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for uronate dehydrogenase genes, techniques known to those of ordinary skill in the art such as Southern blots, Northern blots and amplification protocols such as polymerase chain reaction using primers which hybridize to the sequences presented can be applied.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating uronate dehydrogenase polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as uronate dehydrogenase enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated polypeptides encoded by the foregoing uronate dehydrogenase nucleic acids. Such polypeptides are useful, for example, alone or as fusion proteins to convert glucuronic acid to glucaric acid in vivo or in vitro. Uronate dehydrogenase polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Polypeptides can also be synthesized chemically using well-established methods of peptide synthesis.

The invention embraces variants of the uronate dehydrogenase polypeptides described above. As used herein, a "variant" of a uronate dehydrogenase polypeptide is a polypeptide which contains one or more modifications to the primary amino acid sequence of a uronate dehydrogenase polypeptide. Modifications which create a uronate dehydrogenase variant can be made to a uronate dehydrogenase polypeptide 1) to reduce or eliminate an activity of a uronate dehydrogenase polypeptide; 2) to enhance a property of a uronate dehydrogenase polypeptide, such as the ability to convert glucuronic acid to glucaric acid or protein stability in an expression system or the stability of protein-protein binding; 3) to provide a novel activity or property to a uronate dehydrogenase polypeptide, such as addition of an antigenic epitope or addition of a detectable moiety; or 4) to provide equivalent or better binding between a uronate dehydrogenase molecule and another molecule (e.g., an enzymatic substrate). Modifications to a uronate dehydrogenase polypeptide are typically made to the nucleic acid which encodes the uronate dehydrogenase polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the uronate dehydrogenase amino acid sequence. One of skill in the art will be familiar with methods for predicting the effect on protein conformation of a change in protein sequence, and can thus "design" a variant uronate dehydrogenase polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a uronate dehydrogenase polypeptide can be proposed and tested to determine whether the variant retains a desired conformation.

In general, variants include uronate dehydrogenase polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a uronate dehydrogenase polypeptide by eliminating proteolysis by proteases in an expression system (e.g., dibasic amino acid residues in yeast expression systems in which KEX2 protease activity is present).

Mutations of a nucleic acid which encode a uronate dehydrogenase polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant uronate dehydrogenase polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a uronate dehydrogenase gene or cDNA clone to enhance expression of the polypeptide. The activity of variants of uronate dehydrogenase polypeptides can be tested by cloning the gene encoding the variant uronate dehydrogenase polypeptide into a bacterial or mammalian expression vector, introducing the vector into an appropriate host cell, expressing the variant uronate dehydrogenase polypeptide, and testing for a functional capability of the uronate dehydrogenase polypeptides as disclosed herein.

The skilled artisan will also realize that conservative amino acid substitutions may be made in uronate dehydrogenase polypeptides to provide functionally equivalent variants of the foregoing polypeptides, i.e., the variants retain the functional capabilities of the uronate dehydrogenase polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the uronate dehydrogenase polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of uronate dehydrogenase polypeptides to produce functionally equivalent variants of uronate dehydrogenase polypeptides typically are made by alteration of a nucleic acid encoding a uronate dehydrogenase polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a uronate dehydrogenase polypeptide.

The invention as described herein has a number of uses, some of which are described elsewhere herein. First, the invention permits isolation of the uronate dehydrogenase protein molecules. A variety of methodologies well-known to the skilled practitioner can be utilized to obtain isolated uronate dehydrogenase molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating uronate dehydrogenase polypeptides. These include, but are not limited to, immunochromatography, HPLC, size-exclusion chromatography, ion-exchange chromatography and immune-affinity chromatography.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

The invention also provides antibodies against uronate dehydrogenase (Udh). In some embodiments the antibodies bind to a polypeptide comprising at least 95% amino acid identity to SEQ ID NO:2. In some embodiments the antibodies bind to a polypeptide that is encoded by a nucleic acid molecule that has at least 95% nucleotide identity with SEQ ID NO:1. In some embodiments the antibodies bind to a polypeptide comprising at least 95% amino acid identity to SEQ ID NO:24. In some embodiments the antibodies bind to a polypeptide that is encoded by a nucleic acid molecule that has at least 95% nucleotide identity with SEQ ID NO:23. In some embodiments the antibodies bind to a polypeptide comprising at least 95% amino acid identity to SEQ ID NO:26. In some embodiments the antibodies bind to a polypeptide that is encoded by a nucleic acid molecule that has at least 95% nucleotide identity with SEQ ID NO:25.

The antibodies of the present invention are prepared by any of a variety of methods, including administering a protein, fragments of a protein, cells expressing the protein or fragments thereof and the like to an animal to induce polyclonal antibodies. The present invention also provides methods of producing monoclonal antibodies to Udh. The production of monoclonal antibodies is performed according to techniques well known in the art. It is well-known in the art that only a small portion of an antibody molecule, the paratope, is involved in the binding of the antibody to its epitope (see, in general, Clark, W. R., 1986, The Experimental Foundations of Modern Immunology, Wiley & Sons, Inc., New York; Roitt, I., 1991, Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762, and 5,859,205. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans. Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies, domain antibodies and heavy chain antibodies.

It should be appreciated that the genes encoding uronate dehydrogenase, myo-inositol 1-phosphate synthase and myo-inositol oxygenase can be obtained from a variety of sources. In the embodiments discussed in the Example section presented herein, the myo-inositol 1-phosphate synthase enzyme is encoded by a gene from *Saccharomyces cerevisiae* (INO1), the myo-inositol oxygenase enzyme is encoded by a mouse gene (MIOX) and the uronate dehydrogenase enzyme is encoded by a *Pseudomonas syringae, Pseudomonas putida*, or *Agrobacterium tumefaciens* gene (udh). As one of ordinary skill in the art would be aware, homologous genes for these enzymes exist in many species and can be identified by homology searches, for example through a protein BLAST search, available at the NCBI internet site (www.ncbi.nlm.nih.gov). Genes encoding for these enzymes can be PCR amplified from DNA from any source which contains the given enzyme, for example using degenerate primers, as would be understood by one of ordinary skill in the art. In some embodiments, the gene encoding for a given enzyme can be synthetic. Any means of obtaining the genes encoding for the enzymes discussed here are compatible with constructing the pathways of the instant invention.

EXAMPLES

Example 1

Glucaric Acid Production: Biosynthetic Pathway in Recombinant *Escherichia coli*

A synthetic pathway has been constructed for the production of glucuronic and glucaric acids from glucose in *Escherichia coli* (FIG. 1). Co-expression of the genes encoding myo-inositol-1-phosphate synthase (Ino1) from *Saccharomyces cerevisiae* and myo-inositol oxygenase (MIOX) from mouse led to production of glucuronic acid through the intermediate myo-inositol. Glucuronic acid concentrations up to 0.3 g/L were measured in the culture broth. The activity of MIOX was rate-limiting, resulting in the accumulation of both myo-inositol and glucuronic acid as final products, in approximately equal concentrations. Inclusion of a third enzyme, uronate dehydrogenase (Udh) from *Pseudomonas syringae*, facilitated the conversion of glucuronic acid to glucaric acid. The activity of this recombinant enzyme was more than two orders of magnitude higher than that of Ino1 and MIOX and increased overall flux through the pathway such that glucaric acid concentrations in excess of 1 g/L were observed. This represents a novel microbial system for the biological production of glucaric acid, a "top-value added chemical" from biomass.

Materials and Methods

Strains, Growth Media, and Plasmids.

*E. coli* strain DH10B [F⁻ mcrA Δ(mrr-hsdRMS-mcrBC) φ80lacZΔM15 ΔlacX74 recA1 endA1 araΔ139 Δ(ara, leu) 7697 galU galK λ-rpsL (Str$^R$) nupG] was used for all molecular biology manipulations. DH10B and BL21 Star™ (DE3) [F⁻ ompT hsdS$_B$ ($r_B^{-m}$$_B^-$) gal dcm rne131 (DE3)] were used as hosts for production of organic acids. Competent cells of both strains were purchased from Invitrogen Corporation (Carlsbad, Calif.). Cultures were propagated in either LB or M9 media. LB (Miller) medium was prepared from dehydrated powder according to manufacturer's instructions (BD Biosciences, San Jose, Calif.). M9 was prepared as described (32), and consisted of lx M9 salts (12.8 g/L Na$_2$HPO$_4$.7H$_2$O, 3 g/L KH$_2$PO$_4$, 0.5 g/L NaCl, 1 g/L NH$_4$Cl, 2 mM MgSO$_4$, 0.1 mM CaCl$_2$, and 10 g/L (1%) glucose. Leucine was added to a final concentration of 105 μg/mL for DH10B. Kanamycin was added to a final concentration of 20 μg/mL and ampicillin to a final concentration of 100 μg/mL where desired to provide selective pressure for plasmid maintenance.

All molecular biology manipulations were performed according to standard practices (32). The INO1 gene encoding myo-inositol 1-phosphate synthase (Ino1, also known as MIPS) was PCR-amplified from a genomic DNA preparation of *Saccharomyces cerevisiae* using the following primers: forward—5'-GAATTCATGACAGAAGATAATATTGCTC-3'(SEQ ID NO:3); reverse—5'-AAGCTTCTACAACAATCTCTCTTCG-3' (SEQ ID NO:4). EcoRI and HindIII restriction sites included in the 5' ends of the primers are underlined. The mouse MIOX gene encoding myo-inositol oxygenase was synthesized with codon optimization for expression in *E. coli* by DNA 2.0 (Menlo Park, Calif.) based on GenBank Accession Number AF197127. Optimization of the 858 nucleotide (286 codon) sequence was performed by the vendor, with the results summarized as follows: 19.2% of the nucleotides were altered, affecting 153 of the 286 codons (53.5%). Among the optimized codons, 144 (94.1%) were only altered at the third nucleotide position. All three nucleotides were changed in 3 of the codons. The synthetic gene was received as plasmid pJ2-MIOX. EcoRI and HindIII restriction sites were included in the 5' and 3' ends of the gene, respectively. A sequence alignment of the mouse MIOX gene and its synthesized version with codon optimization for expression in *E. coli* is presented in FIG. 4. Both genes were sub-cloned into the IPTG-inducible plasmids pMMB206 (25) and pTrc99A (2) to confirm activity of the expressed enzymes. The resulting plasmids were designated pMMB-INO1, pTrc-INO1, pMMB-MIOX, and pTrc-MIOX. For co-expression of both genes, the pRSFDuet-1 vector from Novagen containing two T7 promoters was used (Gibbstown, N.J.). The INO1 gene was sub-cloned into the first position using the EcoRI and HindIII sites, producing plasmid pRSFD-IN. To introduce the MIOX gene into the second position, the HindIII site of pJ2-MIOX was end-filled using Klenow enzyme prior to digestion with EcoRI. pRSFD-IN was first digested with XhoI and end-filled and then digested with the EcoRI-compatible MfeI prior to ligation with the MIOX gene fragment. The resulting plasmid was designated as pRSFD-IN-MI. Isolation of the udh gene encoding uronate dehydrogenase from *Pseudomonas syringae* (GenBank Accession Number EU377538) is presented in Example 2. The udh gene from *Pseudomonas syringae* was sub-cloned into pTrc99A to produce pT1053 (hereafter referred to as pTrc-udh) as described (40).

Enzyme Assays for MIPS (INO1), MIOX, and UDH Activity.

Functional expression of the INO1, MIOX, and udh genes was confirmed through in vitro assays of enzyme activity. Crude lysates were prepared by first re-suspending cell pellets from 1-2 mL culture in 100-200 μl, 10 mM Tris-Cl (pH 8.0) with 1 mg/mL lysozyme. Cell solutions were lysed by alternating freezing in liquid nitrogen with thawing in 30-40° C. water for 5 cycles. The resulting solutions were centrifuged at 14,000 rpm at 4° C. for 15 minutes to remove insolubles. The total protein concentration of lysates was determined using the Bradford method (11).

Assays for myo-inositol 1-phosphate synthase activity were performed as described previously (1, 6). Briefly, glucose-6-phosphate substrate was converted to myo-inositol-1-phosphate in a reaction buffer consisting of 50 mM Tris-acetate (pH 7.5), 0.8 mM NAD$^+$, 14 mM NH$_4$Cl, 5 mM mercaptoethanol, and 5 mM glucose-6-phosphate. Reactions were initiated with the addition of lysate and incubated for 1 hr at 37° C. Reactions were terminated with the addition of 0.4 volume 20% trichloroacetic acid. To quantitate product, inorganic phosphate was removed from the myo-inositol-1-phospate by oxidation with equal volume 0.2 M NaIO$_4$. Excess periodate was destroyed with the addition of equal volume 1 M Na$_2$SO$_3$. Control reactions were established without glucose-6-phosphate and without addition of periodate.

Assays for myo-inositol oxygenase activity were performed as described previously (4, 30, 31). The reaction buffer consisted of 50 mM Tris-Cl (pH 8.0), 2 mM L-cysteine, 1 mM Fe(NH$_4$)$_2$(SO$_4$)$_2$, and 60 mM myo-inositol. Samples were pre-incubated without substrate for 10 minutes at 30° C. to activate the MIOX enzyme. Reactions were incubated for 1 hr at 30° C., then terminated with the addition of ⅒ volume 30% trichloroacetic acid. The glucuronic acid produced was quantified using an orcinol reagent (13). The reagent consisted of 40 mg orcinol in 10 mL concentrated HCl containing 5.4 mg FeCl$_3$. One volume sample was mixed with two volumes orcinol reagent and incubated for 30 minutes in boiling water. After cooling to room temperature, absorbance at 670 nm was measured to determine glucuronic acid concentration. Control reactions were established without myo-inositol to account for background.

Assays for uronate dehydrogenase activity were performed by monitoring NADH co-factor generation at 340 nm as described previously (35, 40). The reaction mixture contained 100 mM sodium phosphate buffer (pH 8.0), 2.5 mM glucuronic acid, 0.9 mM NAD$^+$, and bacterial lysate prepared as described above.

Growth Conditions for Acid Production.

Cultures were grown in LB medium supplemented with 10 g/L glucose and induced with IPTG as indicated in Results. An inoculum was prepared in LB medium, and 1 or 2% (v/v) was used to inoculate 250-mL baffled flasks containing 50 or 100 mL of medium. The cultures were incubated at 30° C. and 250 rpm, with periodic sampling to determine cell density and product concentration in the culture medium.

Detection and Quantification of Organic Acids.

Metabolites including glucuronic acid and glucaric acid were quantified by high-performance liquid chromatography (HPLC). For glucaric acid assays, samples were pre-treated as previously described (28, 40) to separate glucaric acid from other metabolites including glucuronic acid. Briefly, boronic acid affinity gel (Affi-gel boronate gel, Bio-Rad Laboratories, Hercules, Calif.), which has an affinity for the coplanar adjacent cis-hydroxyl groups present in glucaric acid (28), was mixed with samples and washed with 80 mM potassium phosphate-20 mM boric acid buffer (pH 7.0). Glucaric acid was eluted with 0.1 M hydrochloric acid. The eluate was neutralized by adding 10 M NaOH and then analyzed by HPLC. HPLC analyses were performed on an Agilent 1100 series instrument equipped with an Aminex HPX-87H column (300 mm×7.8 mm, Bio-Rad Laboratories, Hercules, Calif.) and refractive index and diode array detectors under the following conditions: mobile phase, 5 mM sulfuric acid in water; flow rate, 0.5 mL/min; injection volume, 50 µL; temperature, 55° C.; UV wavelength, 210 nm.

Results

Verification of Recombinant Ino1 and MIOX Activities.

The use of myo-inositol 1-phosphate synthase (Ino1) from *Saccharomyces cerevisiae* to produce high concentrations of myo-inositol through *E. coli* fermentation has been previously reported (15). Product titers up to 21 g/L were obtained under high cell density, fed-batch fermentations operated for 54 hrs. To confirm Ino1 performance in shake flasks, the corresponding gene was amplified, inserted into a compatible vector, then sub-cloned into both high- and medium-copy plasmids for expression in the common laboratory strain DH10B. Plasmid pTrc-INO1 contains the modified ColE1 replicon that results in copy numbers of several hundred, while pMMB-INO1 is based on the RSF1010 replicon with a copy number of the order of 10. Two plasmids were evaluated to explore the potential for co-expression of the INO1 and MIOX genes in a single strain using compatible vectors. In vitro activity of 344 nmol/hr/mg and 128 nmol/hr/mg was measurable for cultures harboring pTrc-INO1 and pMMB-INO1, respectively, and incubated at 30° C., indicating successful expression of the enzyme (Table 1). However, only expression from the high-copy plasmid resulted in accumulation of measurable quantities of myo-inositol in the culture medium, 0.37 g/L. Activity was also a strong function of temperature, with none detectable for cultures grown at 37° C. myo-Inositol production was also tested in M9 minimal medium. It was postulated that growth in minimal medium with glucose as the only carbon source might increase glucose flux and accordingly increase myo-inositol production. However, only half the amount of myo-inositol was produced, suggesting that while glucose flux may indeed be higher, the Ino1 enzyme expressed under these conditions does not compete as effectively against glycolysis for substrate. Subsequent experiments were conducted in LB medium supplemented with glucose.

MIOX is a protein of primarily eukaryotic origin, and the homologues from human, mouse, rat, and pig have been best characterized (3, 4, 30, 31). myo-Inositol oxygenase (MIOX) has been functionally expressed in *E. coli* and purified for characterization of the enzyme's properties; however, to our knowledge, mammalian MIOX has not been used in a whole cell, recombinant system to produce glucuronic acid. The mouse version of the enzyme had been found to have the most favorable properties upon expression in *E. coli* (3) and was chosen for investigation. A synthetic version of the gene was purchased from DNA 2.0, with codon optimization for *E. coli*. This gene was also sub-cloned into both the high-copy and low-copy vectors used to evaluate Ino1 activity in DH10B. MIOX activity was initially evaluated at 37° C. since the enzyme is of mammalian origin.

The MIOX enzyme is known to require $Fe^{2+}$ and cysteine for activation in vitro (4). The addition of these compounds to the culture medium did not improve the expression of the enzyme from pTrc-MIOX as measured in the in vitro assay but rather resulted in a decrease in activity (Table 2). Glucuronic acid was still measured in the culture medium, though at a lower concentration. The observed decrease in enzyme activity coincided with a significant decrease in cell density, indicating toxicity of these compounds to the host. As reported previously (30, 31), MIOX activity is inhibited by $Fe^{2+}$ and cysteine at high concentrations. While the extracellular concentrations were set at a level that activates the enzyme in the in vitro assay, the corresponding intracellular concentrations are unknown. It was also reported previously that inclusion of myo-inositol in the culture medium improved soluble expression of MIOX in *E. coli* (3). This behavior was also observed herein, noting a sharp decrease in activity of the enzyme when expressed in the absence of myo-inositol supplementation (Table 2). One striking feature of recombinant MIOX is its apparent instability (3). High activity was observed in samples taken during exponential phase (6 hrs after inoculation) but dropped substantially in stationary phase (24 hrs after inoculation) (Table 2). The background activity of the assay, as measured in control samples containing empty pTrc99A plasmid, generally increases with time. Note that the high background of the assay results from the non-specificity of the orcinol reagent, which is known to react with other biological compounds, though to a smaller extent. As a result, the assay may not be reliable for precise quantification of enzyme activity. However, the differences observed between samples with and without myo-inositol, and between samples with myo-inositol at early and late time points are sufficiently large that the trends can be considered significant. Neither in vitro enzyme activity nor in vivo production of glucuronic acid was observed in cultures containing the lower copy pMMB-MIOX construct, suggesting that high expression levels are required to achieve measurable MIOX activity. Because INO1 is only actively expressed at 30° C., in vivo MIOX performance was also evaluated at this temperature from the high copy plasmid. A comparable amount of glucuronic acid, 0.40 g/L, was produced after 24 hr in culture, with titers doubling to 0.78 g/L after 48 hr.

Production of Glucuronic Acid.

Production of glucuronic acid from glucose requires the co-expression of both INO1 and MIOX in the same strain. The compatible plasmids pTrc99A and pMMB206 were both investigated, with the expectation that a doubly transformed strain containing either pTrc-INO1 and pMMB-MIOX or pMMB-INO1 and pTrc-MIOX could be used for production. However, our results indicated that reasonable in vivo activities, as determined by accumulation of each desired product in the culture medium, were only achievable with expression of both genes from high-copy plasmids. To address this issue, we introduced both enzymes into the high-copy pRSFDuet vector, which contains a pair of multi-cloning sites, each behind a T7 promoter. Enzyme activities were confirmed as described previously and expression was verified by SDS-PAGE (data not shown). In this manner, an IPTG concentration of 0.1 mM was determined to be preferred. The host strain was also changed from DH10B to BL21(DE3), to enable expression from the T7 promoter. We had previously observed that DH10B was incapable of consuming glucuronic acid for growth (data not shown). BL21(DE3) can metabolize glucuronic acid; however, its consumption appeared to be subject to catabolite repression (data not shown). Therefore, cultivation of the strain in excess glucose prevents consumption of the desired product.

Figure 2:
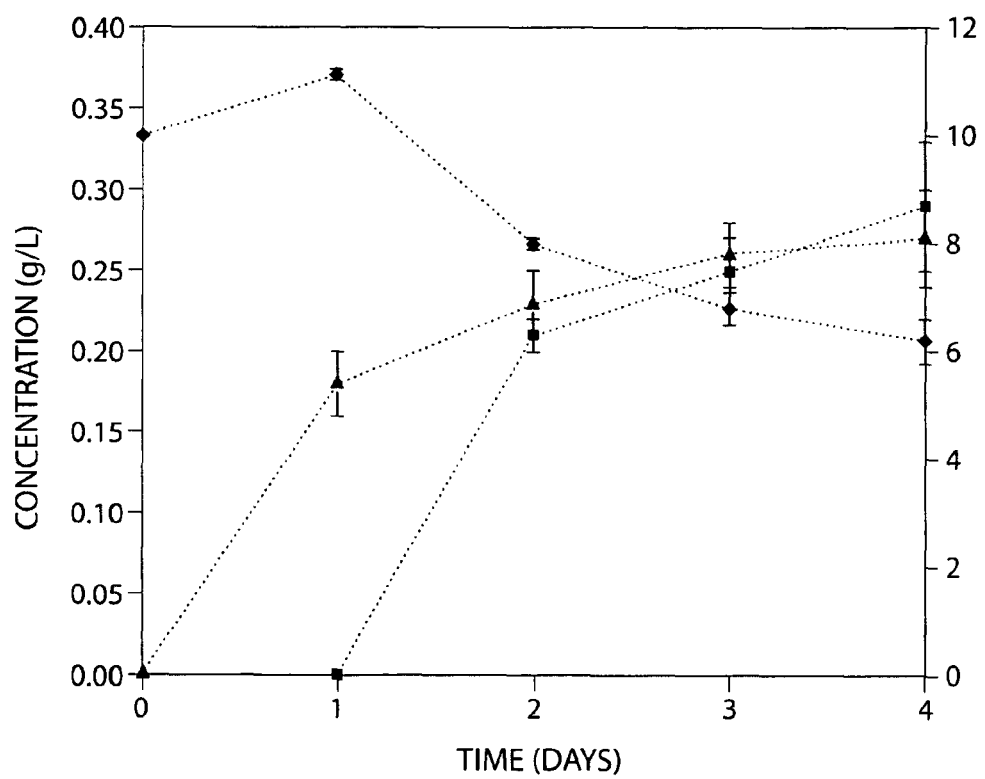
FIG. 2 is a graph showing production of glucuronic acid in BL21(DE3)(pRSFD-IN-MI). Cultures were grown in triplicate at 30° C. in LB medium supplemented with 10 g/L glucose and 0.1 mM IPTG. Data points are the average and standard deviation of the three biological replicates. Δ=Glucuronic acid (left axis); □=Myo-inositol (left axis); ◊=Glucose (right axis). Glucose concentration is in g/L.

The BL21(DE3) strain carrying pRSFD-IN-MI was capable of producing glucuronic acid from glucose, though to levels of only ~270 mg/L (FIG. 2). The culture profile shows that glucuronic acid was present after 24 hrs with no intermediates detectable, and the concentration increased by 50% in 4 days. However, after 48 hr, significant quantities of myo-inositol appeared in the culture medium. myo-Inositol continued to accumulate in the medium and was present in concentrations slightly higher than the desired end product, glucuronic acid, by the end of the experiment. The final glucuronic acid concentration, 0.27 g/L, was lower than that observed with direct conversion of myo-inositol in the DH10B (pTrc-MIOX) system above (0.78 g/L). The accumulation of myo-inositol suggests that MIOX activity is the limiting factor in production of high concentrations of glucuronic acid. In vitro assays confirmed that Ino1 activity was significantly higher than the vector-only control throughout the course of the experiment, with only marginal background activity appearing after 3 days (data not shown). In contrast, MIOX activity was only slightly higher than background after 1 day and was subsequently indistinguishable from background. This is consistent with the results summarized previously (Table 2) that indicate that MIOX activity drops sharply after 24 hrs. Additionally, it is likely that the activity of MIOX in this system is limited by the concentration of myo-inositol produced by Ino1. While an extracellular supplementation of 60 mM (10.8 g/L) myo-inositol does not mean the intracellular concentration is also this high, it is reasonable to suspect that the intracellular concentrations of myo-inositol that result from Ino1 activity are likely to fall short of the equivalent concentration.

Production of Glucaric Acid.

Figure 3:
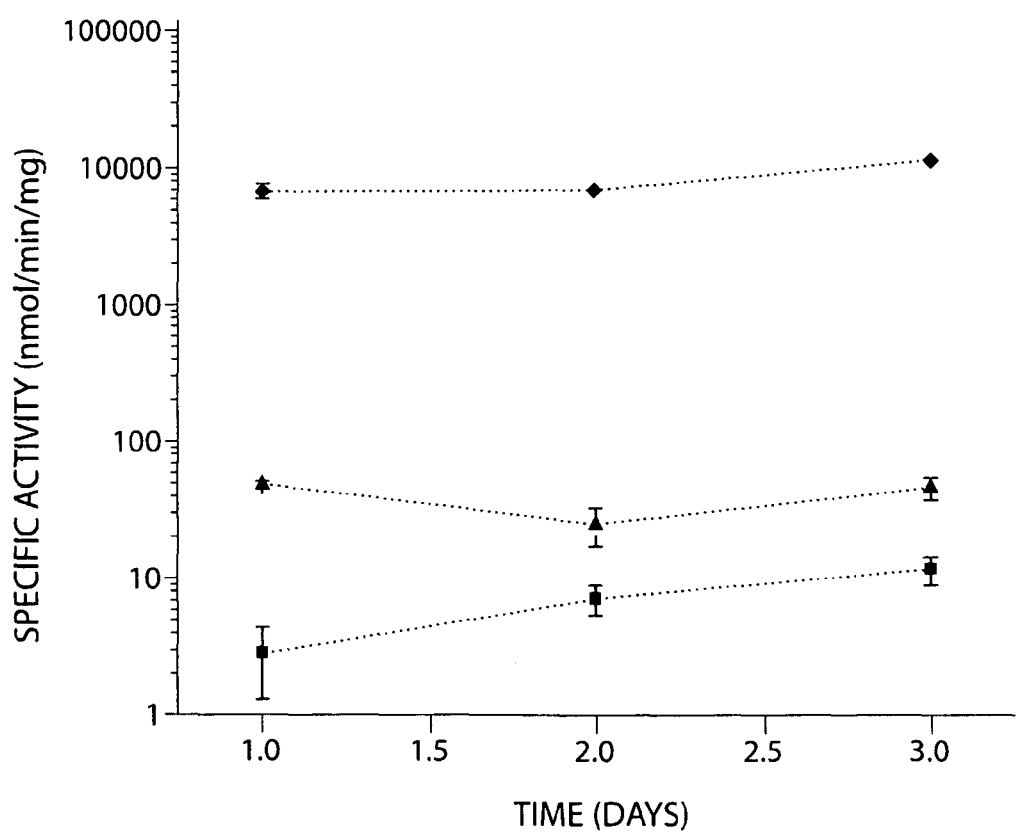
FIG. 3 is a graph showing in vitro activity of recombinant Ino 1, MIOX, and Udh expressed in BL21(DE3) harboring the three genes. Cultures were grown at 30° C. in LB medium supplemented with 10 g/L glucose and induced with 0.05 mM IPTG. Cell lysates were prepared at each time point indicated, and enzyme activities represent measurements within the cell lysate mixture. MIOX activity is presented as net activity to account for background. Data are the average and standard deviation of the three biological replicates. Δ=Ino 1; □=MIOX; ◇=Udh. For measurement of Ino 1 activity, glucose-6-phosphate was supplied as a substrate to produce myo-inositol-1-phosphate as a product. For measurement of MIOX activity, myo-inositol was provided as a substrate to produce glucuronic acid as a product. For measurement of Udh activity, glucuronic acid was provided as a substrate to produce glucaric acid as a product.

Example 2 reveals cloning and characterization of the gene encoding uronate dehydrogenase activity from *Pseudomonas syringae* pv. tomato DC3000 (40). The udh gene was found to be very well-expressed in *E. coli*, resulting in high enzyme activities. For the production of glucaric acid, we utilized a previously constructed vector harboring the udh gene in pTrc99A, which is compatible with pRSFD-IN-MI. Both vectors were introduced into BL21(DE3) to construct an *E. coli* strain carrying INO1, MIOX, and udh. Productivity of this strain was measured under several different induction conditions (Table 3). To our surprise, up to 1 g/L of glucaric acid was produced although only 0.27 g/L of glucuronic acid was previously observed in the system harboring the first two genes. Under induction conditions identical to those previously used for glucuronic acid (Table 3, Condition A), 0.72 g/L of glucaric acid was produced. To further characterize the system, enzyme activities in crude lysates were measured after each day of culture (FIG. 3). Udh activity was highest, more than two orders of magnitude higher than Ino1 activity, and three orders of magnitude higher than MIOX activity. The high activity of Udh thus appears to pull glucose flux through the glucaric acid pathway, leading to a relatively higher titer of glucaric acid. In these samples, MIOX activity does not appear to decrease over time as observed previously; however, the magnitude of the activity remains quite low. Additionally, the first data point here is after one day, when MIOX activity was previously shown to have decreased significantly from that observed during exponential growth (Table 2). No glucuronic acid was detected after three days culture time while myo-inositol accumulated, confirming that the MIOX-catalyzed step is limiting.

The three induction conditions tested resulted in glucaric acid concentrations that ranged from 0.72 to 1.13 g/L. In general, higher induction levels, i.e., higher IPTG concentration, resulted in a higher yield of glucaric acid on glucose but lower product concentration (compare, for example, Conditions A and B in Table 3). Higher induction levels also led to less glucose consumption and a lower cell density, indicating a metabolic burden associated with higher expression of the three enzymes. However, in the case of lower glucose consumption rate, a higher fraction of glucose flux was directed towards glucaric acid production versus biomass. We also observed that poorer aeration, resulting from doubling the total culture volume from 50 to 100 mL in 250-mL baffled flasks, led to a decrease in the glucaric acid titer by half, while growth was not affected (data not shown). This reduced titer is likely attributed to the fact that MIOX, the enzyme for the limiting step, uses molecular oxygen as a co-substrate (12, 38). Finally, production of glucaric acid was tested in M9 minimal medium; however, a negligible amount of glucaric acid was produced.

Discussion

Demonstrated herein is the assembly of a biosynthetic pathway for the production of glucaric acid using enzymes from three disparate sources: Ino1 from *S. cerevisiae*, MIOX from mouse, and Udh from *P. syringae*. An endogenous phosphatase also participates in the pathway. The suhB gene product of *E. coli* has been shown to possess inositol monophosphatase activity in vitro and is therefore a reasonable candidate for this endogenous activity (23). This pathway is attractive from a thermodynamics perspective, since the standard free energy changes ($\Delta G$) for all three steps, as estimated by group contribution theory (21, 24) and considering molecular oxygen as the ultimate oxidant, are all negative: −14.3 Kcal/mol for the glucose to myo-inositol step; −86.8 Kcal/mol for the myo-inositol to glucuronic acid step; −55.9 Kcal/mol for the glucuronic to glucaric acid step. However, as Khosla and Keasling have indicated (18), metabolic engineering is more than simply recruiting various enzymes. It also involves global optimization of metabolic flux when perturbations such as the introduction of new pathways into a host organism are made. Issues of metabolic burden associated with the maintenance of plasmids and expression of plasmid-encoded genes are of particular interest in this case (9, 10, 17). In our system, a detectable amount of glucuronic acid was produced in vivo only by high-copy number plasmids. Glucose-6-phosphate, the first substrate, should not be limiting for central metabolism because LB medium supplemented with excess glucose was used for growth. Therefore, it appears that high expression levels of the recombinant genes are needed in order to compete with the fast and robust glycolysis pathway and to divert glucose-6-phosphate towards glucuronic acid. The result that only small amounts of myo-inositol and no detectable amount of the organic acids was produced in M9 medium implies that when glucose is the sole carbon and energy source, almost all of the substrate enters endogenous cellular metabolism. This competition may also explain why the yield of glucaric acid on glucose during the first two days of the process, when glucose concentration is higher in the medium, is generally higher than that of the later days when the concentration is lower (data not shown). The requirement for myo-inositol to achieve high MIOX activity suggests that low productivity from the Ino1 enzyme may ultimately be the limitation towards formation of the organic acids in M9 medium. Alternatively, MIOX may be poorly expressed in minimal medium. It should be noted that previous studies with Ino1 have resulted in high levels of myo-inositol production in an alternative chemically-defined medium and also employing a high-copy number plasmid for gene expression; however, these experiments were conducted in larger-scale, fed-batch fermentations for several days (15). During the initial batch period prior to the onset of glucose feeding (approximately 10 hours), the myo-inositol concentration was less than 1 g/L. Thus, it is worth exploring the extent to which cultivation under fed-batch conditions could improve the productivity of our system.

Plasmid copy number is not the only factor related to expression level that affects the performance of our synthetic system. As shown in Table 3, increasing the inducer concentration to increase expression resulted in lower product concentration. IPTG concentrations below 0.05 mM did not improve glucaric acid production even though glucose consumption rate and growth rate were enhanced due to the reduced metabolic burden (data not shown). E. coli growth is better at 37° C. than at 30° C. and the activity of the rate-limiting enzyme MIOX should be higher at 37° C. However, fermentation was performed at 30° C. because Ino1 was only functionally expressed at this lower temperature. Considering the reported unusual thermal instability of Udh (7, 35), a temperature lower than 30° C. may be better for its activity; however, we observed that the Udh activity at 30° C. was much higher than that of either Ino1 or MIOX (FIG. 3) and selected 30° C. as the culture temperature to maximize the functional expression of Ino1.

In considering overall limitations on productivity of this system, potential inhibition by intermediates in the pathway should be examined. MIOX from hog kidney was reported to be inhibited in vitro by D-glucaric acid but not by D-glucuronate and D-glucuronolactone (30, 31). Given that MIOX activity dropped sharply at the stationary phase even in the absence of D-glucaric acid (Table 2), low MIOX activity is more likely due to its intrinsic instability than inhibition by intermediates (3). It should also be noted that we did not overexpress the suhB gene or a homologous phosphatase. However, no myo-inositol-1-phosphate was detected among the culture products, while myo-inositol did accumulate. Therefore, we conclude that the phosphatase activity is not limiting flux through the pathway. E. coli also contains the D-glucarate catabolic pathway (16). Indeed, the ability of E. coli to consume D-glucarate as the sole carbon source for growth was used to develop a screen to identify uronate dehydrogenase activity (40). BL21(DE3) can also metabolize D-glucuronic acid. However, the consumption of both organic acids appears to be subject to catabolite repression, preventing the undesirable loss of products in the presence of glucose (data not shown). The theoretical limit of D-glucaric acid titer therefore seems to be determined by the toxicity of the acids and the kinetics of each step. E. coli growth and glucose consumption were not observed to be affected by the addition of potassium glucarate and sodium glucuronate at concentrations as high as 10 g/L (data not shown); thus, there is room for improvement of titers by focusing on improving the kinetics of the rate-limiting steps. Further optimization for enhancing glucose flux to this synthetic pathway can entail recruiting better enzymes from different sources, engineering these enzymes, and down-regulating the competing pathways.

TABLE 1

Activity of recombinant INO1 expressed from high- (pTrc) and medium-copy (pMMB) plasmids in E. coli.

| Culture | In vitro Activity (nmol/hr/mg) | In vivo Activity (g/L) |
| --- | --- | --- |
| pTrc-INO1 | 344 | 0.37 |
| pMMB-INO1 | 128 | N/D |

Cultures were grown at 30° C. in LB medium supplemented with 10 g/L glucose and either 0.1 mM or 1.0 mM IPTG for pTrc-INO1 and pMMB-INO1, respectively. In vitro activities were determined from crude lysates of samples taken in mid-exponential phase, while in vivo activity is reported as the concentration of myo-inositol in the culture medium after 48 hours. The data shown are representative from a single experiment. N/D = not detectable.

TABLE 2

Activity of recombinant MIOX expressed from high-copy pTrc-MIOX in E. coli under various culture conditions.

| Culture Conditions | Activity at 6 hr (nmol/min/mg) | Activity at 24 hr (nmol/min/mg) | Glucuronic Acid (g/L) |
| --- | --- | --- | --- |
| pTrc99A control | N/D | 82 | N/D |
| +MI | 430 | 76 | 0.44 |
| +MI, +Fe, +Cys | 180 | 42 | 0.33 |
| −MI | 28 | 15 | N/A |

Cultures were grown at 37° C. in LB medium and induced with 1.0 mM IPTG. Glucuronic acid was measured at 24 hr. Supplements: MI = myo-inositol (60 mM, 10.8 g/L), Fe = Fe(NH$_4$)$_2$(SO$_4$)$_2$ (1 mM), Cys = L-cysteine (2 mM). N/D = not detectable. N/A = not measured.

TABLE 3

Production of glucaric acid in BL21 (DE3)(pRSFD-IN-MI)(pTrc-udh) after 3 days culture.

| Condition | OD$_{600}$ | Glucose (g/L) | myo-Inositol (g/L) | Glucuronic Acid (g/L) | Glucaric Acid (g/L) | Yield (%) |
| --- | --- | --- | --- | --- | --- | --- |
| A | 5.10 ± 0.27 | 5.69 ± 0.85 | 0.10 ± 0.02 | N/D | 0.72 ± 0.09 | 17.4 ± 5.1 |
| B | 6.13 ± 0.31 | 1.43 ± 0.81 | 0.18 ± 0.05 | N/D | 1.13 ± 0.17 | 13.1 ± 1.0 |
| C | 5.80 ± 0.39 | 2.47 ± 1.00 | 0.23 ± 0.07 | N/D | 0.82 ± 0.06 | 11.0 ± 2.4 |

Cultures were grown at 30° C. in LB medium supplemented with 10 g/L glucose and induced with IPTG. Data are the average and standard deviation of three independent experiments. OD$_{600}$ = optical density at 600 nm, Glc = glucose, MI = myo-inositol, Curo = glucuronic acid, Car = glucaric acid, Yield (%) = 100 × glucaric acid produced/glucose consumed (mol/mol). Condition A = 0.1 mM IPTG at 0 hr; Condition B = 0.05 mM IPTG at 0 hr; Condition C = 0.05 mM IPTG at 0 hr and 0.1 mM IPTG at 17.5 hr. N/D = not detectable.

References for Example 1

1. Adhikari, J., A. L. Majumder, T. J. Bhaduri, S. DasGupta, and R. L. Majumder. 1987. Chloroplast as a locale of L-myo-inositol-1-phosphate synthase. Plant Physiol. 85:611-614.

2. Amann, E., B. Ochs, and K.-J. Abel. 1988. Tightly regulated tac promoter vectors useful for the expression of unfused and fused proteins in *Escherichia coli*. Gene 69:301-315.
3. Arner, R. J., S. Prabhu, and C. C. Reddy. 2004. Molecular cloning, expression, and characterization of myo-inositol oxygenase from mouse, rat, and human kidney. Biochem. Biophys. Res. Comm. 324:1386-1392.
4. Arner, R. J., S. Prabhu, J. T. Thompson, G. R. Hildenbrandt, A. D. Liken, and C. C. Reddy. 2001. myo-Inositol oxygenase: molecular cloning and expression of a unique enzyme that oxidizes myo-inositol and D-chiro-inositol. Biochem. J. 360:313-320.
5. Bailey, J. E. 1991. Toward a science of metabolic engineering. Science 252:1668-1675.
6. Barnett, J. E. G., R. E. Brice, and D. L. Corina. 1970. A colorimetric determination of inositol monophosphatases as an assay for D-glucose 6-phosphate-1 L-myo-inositol 1-phosphate cyclase. Biochem. J. 119:183-186.
7. Bateman, D. F., T. Kosuge, and W. W. Kilgore. 1970. Purification and properties of uronate dehydrogenase from *Pseudomonas syringae*. Arch. Biochem. Biophys. 136:97-105.
8. Benner, S. A. 2003. Synthetic biology: Act natural. Nature 421:118.
9. Bentley, W. E., N. Mirjalili, D. C. Andersen, R. H. Davis, and D. S. Kompala. 1990. Plasmid-encoded protein: The principal factor in the metabolic burden associated with recombinant bacteria. Biotechnol. Bioeng. 35:668-681.
10. Birnbaum, S., and J. E. Bailey. 1991. Plasmid presence changes the relative levels of many host cell proteins and ribosome components in recombinant *Escherichia coli*. Biotechnol. Bioeng. 37:736-745.
11. Bradford, M. M. 1976. A rapid and sensitive method for the quantitation of microgram quantities of protein utilizing the principle of protein-dye binding. Anal. Biochem. 72:248-54.
12. Charalampous, F. C. 1959. Biochemical studies on inositol. V. Purification and properties of the enzyme that cleaves inositol to D-glucuronic acid. J. Biol. Chem. 234:220-227.
13. Charalampous, F. C., and C. Lyras. 1957. Biochemical studies on inositol. IV. Conversion of inositol to glucuronic acid by rat kidney extracts. J. Biol. Chem. 228:1-13.
14. Dean-Johnson, M., and S. A. Henry. 1989. Biosynthesis of inositol in yeast: primary structure of myo-inositol-1-phosphate synthase (EC 5.5.1.4) and functional analysis of its structural gene, the INO1 locus. J. Biol. Chem. 264:1274-1283.
15. Hansen, C. A., A. B. Dean, K. M. Draths, and J. W. Frost. 1999. Synthesis of 1,2,3,4-tetrahydroxybenzene from D-glucose: exploiting myo-inositol as a precursor to aromatic chemicals. J. Am. Chem. Soc. 121:3799-3800.
16. Hubbard, B. K., M. Koch, D. R. Palmer, P. C. Babbitt, and J. A. Gerlt. 1998. Evolution of enzymatic activities in the enolase superfamily: characterization of the (D)-glucarate/galactarate catabolic pathway in *Escherichia coli*. Biochemistry 37:14369-14375.
17. Jones, K. L., S. W. Kim, and J. D. Keasling. 2000. Low-copy plasmids can perform as well as or better than high-copy plasmids for metabolic engineering of bacteria. Metab. Eng. 2:328-338.
18. Khosla, C., and J. D. Keasling. 2003. Metabolic engineering for drug discovery and development. Nat. Rev. Drug Discov. 2:1019-1025.
19. Kiely, D. E., L. Chen, and T. H. Lin. 1994. Simple preparation of hydroxylated nylons—polyamides derived from aldaric acids. ACS Sym. Ser. 575:149-158.
20. Kuellmer, V. 2001. Ascorbic acid, Kirk-Othmer Encyclopedia of Chemical Technology, 4th ed. John Wiley & Sons.
21. Li, C., C. S. Henry, M. D. Jankowski, J. A. Ionita, V. Hatzimanikatis, and L. J. Broadbelt. 2004. Computational discovery of biochemical routes to specialty chemicals. Chem. Eng. Sci. 59:5051-5060.
22. Martin, V. J., D. J. Pitera, S. T. Withers, J. D. Newman, and J. D. Keasling. 2003. Engineering a mevalonate pathway in *Escherichia coli* for production of terpenoids. Nat. Biotechnol. 21:796-802.
23. Matsuhisa, A., N. Suzuki, T. Noda, and K. Shiba. 1995. Inositol monophosphatase activity from the *Escherichia coli* suhB gene product. J. Bacteriol. 177:200-205.
24. Mavrovouniotis, M. L. 1991. Estimation of standard Gibbs energy changes of biotransformations. J. Biol. Chem. 266:14440-14445.
25. Morales, V. M., A. Backman, and M. Bagdasarian. 1991. A series of wide-host-range low-copy-number vectors that allow direct screening for recombinants. Gene 97:39-47.
26. Nakamura, C. E., and G. M. Whited. 2003. Metabolic engineering for the microbial production of 1,3-propanediol. Curr. Opin. Biotechnol. 14:454-459.
27. Niu, W., M. N. Molefe, and J. W. Frost. 2003. Microbial synthesis of the energetic material precursor 1,2,4-butanetriol. J. Am. Chem. Soc. 125:12998-12999.
28. Poon, R., D. C. Villeneuve, I. Chu, and R. Kinach. 1993. HPLC determination of D-glucaric acid in human urine. J. Anal. Toxicol. 17:146-150.
29. Postma, P. W., J. W. Lengeler, and G. R. Jacobson. 1993. Phosphoenolpyruvate:carbohydrate phosphotransferase systems of bacteria. Microbiol. Rev. 57:543-594.
30. Reddy, C. C., P. A. Pierzchala, and G. A. Hamilton. 1981. myo-Inositol oxygenase from hog kidney. II. Catalytic properties of the homogeneous enzyme. J. Biol. Chem. 256:8519-8524.
31. Reddy, C. C., J. S. Swan, and G. A. Hamilton. 1981. myo-Inositol oxygenase from hog kidney. I. Purification and characterization of the oxygenase and of an enzyme containing the oxygenase and D-glucuronate reductase. J. Biol. Chem. 256:8510-8518.
32. Sambrook, J., and D. W. Russell. 2001. Molecular cloning: a laboratory manual, 3d ed, vol. 1. Cold Spring Harbor Laboratory Press, Cold Spring Harbor.
33. Singh, J., and K. P. Gupta. 2003. Calcium glucarate prevents tumor formation in mouse skin. Biomed. Environ. Sci. 16:9-16.
34. Singh, J., and K. P. Gupta. 2007. Induction of apoptosis by calcium D-glucarate in 7,12-dimethyl benz[a]anthracene-exposed mouse skin. J. Environ. Pathol. Toxicol. Oncol. 26:63-73.
35. Wagner, G., and S. Hollman. 1976. Uronic acid dehydrogenase from *Pseudomonas syringae*: purification and properties. Eur. J. Biochem. 61:589-596.
36. Walaszek, Z., J. Szemraj, M. Hanausek, A. K. Adams, and U. Sherman. 1996. D-glucaric acid content of various fruits and vegetables and cholesterol-lowering effects of dietary D-glucarate in the rat. Nutr. Res. 16:673-681.
37. Werpy, T., and G. Petersen. 2004. Top value added chemicals from biomass. Volume I: Results of screening for potential candidates from sugars and synthesis gas. In N. R. E. L. (NREL) and P. N. N. L. (PNNL) (ed.).
38. Xing, G., L. M. Hoffart, Y. Diao, K. S. Prabhu, R. J. Arner, C. C. Reddy, C. Krebs, and J. M. Bollinger, Jr. 2006. A 39. Yeh, B. J., and W. A. Lim. 2007. Synthetic biology: lessons from the history of synthetic organic chemistry. Nat. Chem. Biol. 3:521-525.
40. Yoon, S.-H., T. S. Moon, P. Iranpour, A. M. Lanza, and K. J. Prather. 2009. Cloning and characterization of uronate dehydrogenases from two Pseudomonads and *Agrobacterium tumefaciens* strain C58. J. Bacteriol. 191:1565-73.

coupled dinuclear iron cluster that is perturbed by substrate binding in myo-inositol oxygenase. Biochemistry 45:5393-5401.

Example 2

Cloning and Characterization of Uronate Dehydrogenase from *Pseudomonas Syringae* pv. Tomato str. DC3000 and *Agrobacterium tumefaciens* str. C58

Uronate dehydrogenase has been cloned from *Pseudomonas syringae* pv. tomato DC3000, *Pseudomonas putida* KT2440, and *Agrobacterium tumefaciens* str. C58. The genes were identified by using a novel complementation assay employing an *Escherichia coli* mutant incapable of consuming glucuronate as the sole carbon source but capable of growth on glucarate. A shotgun library of *P. syringae* was screened in the mutant *E. coli* by growing transformed cells on minimal medium containing glucuronic acid. Colonies that survived were evaluated for uronate dehydrogenase, which is capable of converting glucuronic acid to glucaric acid. In this manner, a 0.8 Kb open reading frame was identified and subsequently verified as udh. Homologous enzymes were identified in *P. putida* and *A. tumefaciens* based on a similarity search of the sequenced genomes. Recombinant proteins from each of the three organisms expressed in *E. coli* were purified and characterized. For all three enzymes, the turnover number, $k_{cat}$, was higher for glucuronate as a substrate than for galacturonate; however, the Michaelis constant, $K_m$, was lower for galacturonate. The *A. tumefaciens* enzyme was found to have the highest rate constant ($k_{cat}=1.9\times10^2$ on glucuronate), which was more than 2-fold higher than both of the *Pseudomonas* enzymes.

Introduction

Aldohexuronate catabolism in bacteria is reported to involve two different pathways, one initiating with an isomerization step and the other with an oxidation step. In the isomerization pathway, aldohexuronate (glucuronate, galacturonate) is isomerized to ketohexuronate by uronate isomerase and ultimately degraded to pyruvate and 3-phosphoglyceraldehyde. The isomerization pathway has been previously reported to occur in bacteria including *Escherichia coli* (7), *Erwinia carotovora* (18) and *Erwinia hrysanthemi* (15), *Areobacter aerogenes* (9, 23), and *Serratia marcescens* (28). In the oxidation pathway, aldohexuronate is oxidized to aldohexarate by uronate dehydrogenase and further catabolized to pyruvate (2, 5, 7, 9, 18, 19, 24). Uronate dehydrogenase (Udh), the key enzyme of this pathway, has been investigated in two plant pathogen bacteria, *Pseudomonas syringae* and *Agrobacterium tumefaciens*. To date, only limited studies pertaining to the properties of Udh have been reported in the literature (3, 6, 38, 43), and no sequence has yet been identified. Udh is classified as an NAD-linked oxidoreductase (EC 1.1.1.203), with a total molecular weight of about 60,000. It is a homo-dimer composed of two subunits of about 30,000 molecular weight each (38). Udh is a thermally unstable, reversible enzyme, with an optimum pH of about 8.0 (3, 6, 38).

Figure 5:
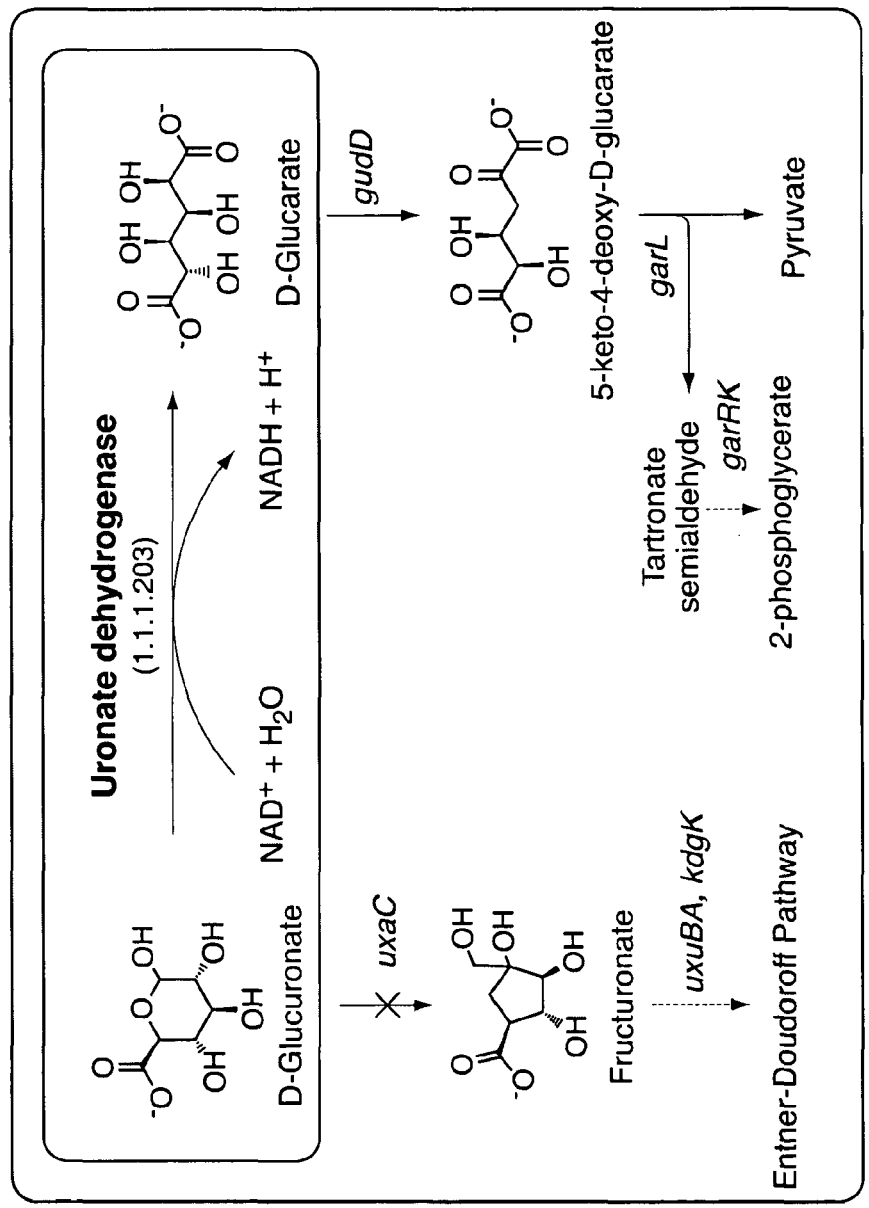
FIG. 5 is a schematic indicating catabolism of glucuronic and glucaric acids in bacteria. Glucuronic acid consumption is prevented by knock-out of the uxaC gene. The presence of uronate dehydrogenase in a uxaC knock-out enables growth of E. coli on glucuronic acid.

In *E. coli* MG1655 with the isomerization pathway for aldohexuronate catabolism, glucuronate is transported by an aldohexuronate transporter encoded by exuT and converted to fructuronate by uronate isomerase, encoded by uxaC (22, 30). Fructuronate is transferred to the Entner-Doudoroff pathway to be utilized as an energy source via 2-keto-3-deoxy-6-phospho-gluconate (7, 27, 31, 32). Therefore, *E. coli* MG1655 with an uxaC deletion can not use glucuronate as a carbon source. In this same strain, glucarate is converted to 5-keto-4-deoxy-D-glucarate by D-glucarate dehydratase, encoded by gudD, and then transferred to glycolysis via pyruvate or 2-phosphoglycerate (27, 33). Recently, a number of bacterial genome sequences have been published, including those of the Udh containing *P. syringae* pv. tomato DC3000 and *A. tumefaciens* str. C58 (4, 10). A shotgun library of *P. syringae* was constructed to identify the gene encoding Udh. Screening for Udh was conducted in *E. coli* MG1655 ΔuxaC. Since uronate dehydrogenase converts glucuronate to glucarate (FIG. 5), *E. coli* ΔuxaC strains harboring the shotgun library of *P. syringae* that can grow in a minimal medium containing glucuronate as a sole carbon source may carry the gene encoding Udh. Once an initial Udh is identified from *P. syringae*, a BLAST homology search may lead to the identification of Udhs from other bacteria.

Materials and Method

Bacterial Strains, Plasmids, and Growth Conditions

Strains, plasmids, and primer sequences used in this study are indicated in Table 4. Media and chemical reagents were purchased from Sigma (St. Louis, Mo., USA) or BD Biosciences (San Jose, Calif., USA). *P. syringae* pv. tomato str. DC3000 was used as the source of the genomic library and was donated by Dr. Frederick Ausubel of Massachusetts General Hospital. *P. syringae* was grown in LB (Luria-Bertani) medium with 50 μg/mL rifampicin at 30° C. *Pseudomonas putida* KT2440 (ATCC 47054) was purchased from the American Type Culture Collection (ATCC, Manassas, Va., USA) and grown in LB medium at 30° C. *E. coli* strains were grown in 2YT medium (16 g tryptone, 10 g yeast extract, and 10 g sodium chloride per liter) at 37° C. As required, ampicillin and kanamycin were added to the medium at 100 and 25 μg/mL, respectively. *Escherichia coli* DH10B (F-mcrA Δ(mrr-hsdRMS-mcrBC) φ80lacZΔM15 ΔlacX74 recA1 endA1 araD139 Δ(ara, leu) 7697 galU galK λ⁻ rpsL nupG) was used as the host strain for the genomic library as well as for subcloning of screened genes (Invitrogen Corp, Carlsbad, Calif., USA). *E. coli* MG1655 ΔuxaC was provided from Dr. F. R. Blattner of the *E. coli* Genome Project at University of Wisconsin-Madison.

For M9 minimal agar, 22 mM glucose, glucuronate, or glucarate were used as carbon sources. Plasmid vectors pTrc99A and pTrc99SE were used for construction of the genomic library and as an expression vector for candidate genes, respectively (Table 4). The plasmid pTrc99SE was donated by Prof Seon-Won Kim at Gyeongsang National University, Korea. pBluescript (Invitrogen, Carlsbad, Calif., USA) was used as a general cloning vector.

Genomic DNA Preparation, Construction and Screening of *P. syringae* Genomic Library Genomic DNA preparation and general cloning procedures were carried out as described in Sambrook et al. (35). The genomic DNA of *A. tumefaciens* str. C58 was purchased from the ATCC (ATCC Number 33970D). Restriction enzymes and T4 ligase were purchased from New England Biolabs (Beverly, MA, USA). *P. syringae* genomic DNA was partially digested with BfuCI, and then loaded onto a 0.8% agarose gel. Fragments of 2-6 Kb were purified from the gel, and then ligated to pTrc99A with dephosphorylated BamHI ends. After ligation for 2 days at 4° C., the reaction mixtures were used to transform *E. coli* DH10B. Successful transformant clones were collected and pooled from agar plates, followed by storage at -80° C. Plasmid pools isolated from the colony pools were used to transform *E. coli* MG1655 AuxaC to screen for Udh activity. Transformed strains were cultured on M9 minimal agar plates with 22 mM glucuronate for 4 days at 30° C. Surviving clones from plates were screened by purifying and sequencing their plasmids. The sequencing results were compared with the genome sequence of *P. syringae* pv. tomato str. DC3000, as reported in GenBank, Accession Number NC_004578(ncbi.nlm.nih.gov/).

Construction of Expression Plasmid Vectors Containing Udh Genes

PCR amplification was carried out using Pfu Turbo AD as described by the manufacturer (Stratagene, La Jolla, Calif., USA). The three candidate genes of iolE, iolB, and PSPTO_1053 were each amplified from the genomic DNA using primers as listed in Table 4. PCR products were blunt-end ligated to EcoRV-digested pBluescriptII, resulting in pBiolE, pBiolB, pBiolEB and pB1053, which were each sequenced to confirm their identities. iolE, iolB, and iolEB were each cleaved by digestion with EcoRI and SalI, and then ligated to pTrc99A digested by same enzymes to construct pTiolE, pTiolB, and pTiolEB, respectively. PSPTO_1053 from pB1053 was cleaved by digestion with NcoI and SacI, and then ligated to pTrc99A digested by the same enzymes, resulting in pT1053.

Putative udh genes from genomic DNA of *A. tumefaciens, P. putida*, and *P. syringae* were amplified using the primer pairs ATudh2-F/ATudh-R, PPudh-F/PPudh-R and PSudh-F/1053-R, respectively (Table 4). PCR products were blunt-end ligated to pBluescriptII digested with EcoRV, resulting in plasmids pBATudh2, pBPPudh and pBPSudh. To construct plasmids pTATudh2, pTPPudh, and pTPSudh, the corresponding genes were excised with EcoRI and SacI from pBATudh2, pBPPudh, and pBPSudh, respectively, and were inserted into the same sites of pTrc99SE.

Protein Purification and Determination of Kinetic Parameters

The udh genes from genomic DNA of *A. tumefaciens, P. putida*, and *P. syringae* were amplified using primers ATuEQ-F/R, PPuEQ-F/R, and PSuEQ-F/R as listed in Table 4. The PCR products were digested with SacI and HindIII and inserted into the same sites of pET21b containing a 6×His-Tag to construct pETATu, pETPPu, and pETPSu, respectively (Table 4). These plasmids were used to transform *E. coli* BL21 (DE3) to use for protein expression. The recombinant *E. coli* BL21 strains were cultivated at 30° C., 250 rpm for 6 hours after IPTG induction. Protein purification was carried out using the ProBond™ Purification System as described by the manufacturer (Invitrogen Corp, Carlsbad, Calif., USA). SDS-PAGE (sodium dodecyl sulfate-polyacrylamide gel electrophoresis) was performed as described in Sambrook et. al. (35). Enzyme activities on substrates of purified proteins were measured by monitoring initial NADH generation at 340 nm and room temperature. Kinetic analysis on glucuronate and galacturonate was carried out using 0 to 10 mM glucuronate or galacturonate and 1.2 mM NAD$^+$ in 100 mM Tris-HCl, pH 8.0. Kinetic analysis on NAD$^+$ was performed using 0 to 2 mM NAD$^+$ and 10 mM glucuronate in 100 mM Tris-HCl, pH 8.0. A series of enzymatic assays were conducted to estimate the initial activity as a function of starting substrate concentration. These data were used to fit the parameters of the Michaelis-Menten kinetic model, $k_{cat}$ and $K_m$, by nonlinear least-squares regression. Nonlinear least-squares regression analyses were performed via the Gauss-Newton method as implemented using the intrinsic Matlab® function nlinfit.

Figure 8A:
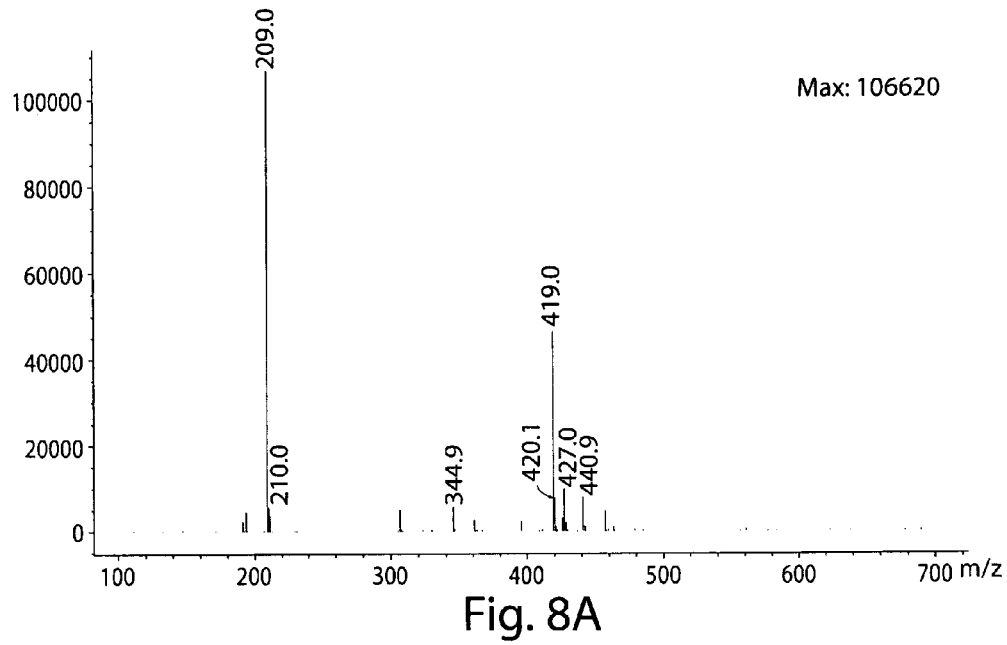
FIG. 8a demonstrates glucarate separated from the enzymatic reaction mixture.
Figure 8B:
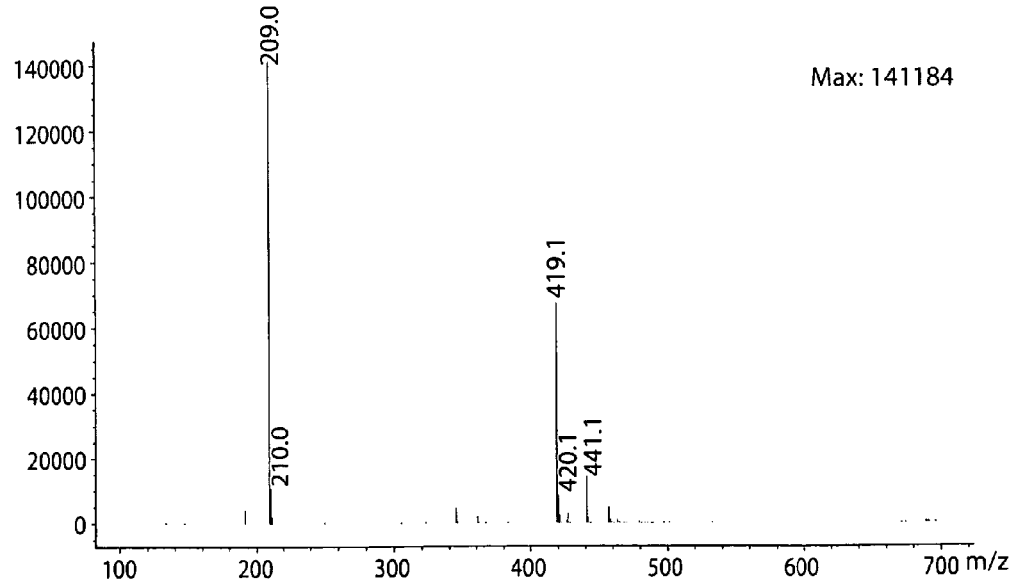
FIG. 8b demonstrates a glucarate standard. Glucarate was characterized by its masses (m/z=209, 210, 419, 420 and 441) and peaks of the eluent also corresponded to masses of glucarate standard.

LC-MS and CD Analysis for Determination of Glucarate Produced from Glucuronate by Udh The reaction mixture for producing glucarate from glucuronate by Udh consisted of 20 mM glucuronate, 21.6 mM NAD$^+$, 40 mM sodium phosphate buffer, pH 8.0, and bacterial lysate prepared as described above. The enzyme reaction was performed by addition of either crude lysate or purified proteins to the reaction mixture and incubation at room temperature for 60 minutes, then stopped by addition of 1M sodium hydroxide. Glucarate was separated from the reaction mixture using a column packed with boronic acid affinity gel (Affi-gel boronate gel, Bio-Rad Laboratories, Hercules, Calif., USA) which is able to bind to the coplanar adjacent cis-hydroxyl groups of glucarate (29). Glucuronate can not bind to the gel due to its trans-diol groups. After loading the Affi-gel column with reaction mixture, the column was washed with 80 mM potassium phosphate-20 mM boric acid buffer (pH 7.0), then glucarate was eluted by the addition of 0.1 M HCl. The eluent was neutralized by the addition of 5 M NaOH then analyzed by LC-MS using an Agilent 1100 series LC/MSD (Agilent Technologies, US) equipped with an Aminex HPX-87H column (300×7.8 mm, Bio-Rad Laboratories, Hercules, Calif. USA) and an electron spray ionization detector. Mass spectra were obtained in both the positive and negative ion detection modes. The spectra shown in FIG. 8 are from the negative ion detection mode. 0.1% (v/v) Trifluoroacetic acid, pH 2.0, was used as the mobile phase at a flow rate of 0.5 mL/min, at room temperature.

The stereochemistry of glucarate formed from glucuronate was confirmed by comparing its circular dichroism (CD) spectrum with that of an authentic glucarate standard. CD was performed on an Aviv Model 202 CD Spectrometer (Aviv Biomedical, Lakewood, N.J.). Reaction mixtures contained 20 mM glucuronic acid, 7 mM NAD$^+$, 100 mM potassium phosphate buffer (pH 8.0), and the purified enzymes prepared as described above. Glucarate was separated from glucuronate using boronic acid affinity gel as described above.

Computational Analysis Including Sequence Identification and Alignment Analysis

Biocyc™ (biocyc.org/) was used to identify relevant metabolic pathways and metabolites. DNA sequences for *P. syringae, P. putida* and *A. tumefaciens*, were obtained from NCBI (National Center for Biotechnology Information; ncbi.nlm.nih.gov/), with Accession Numbers NC_004578, NC_002947 and NC_003063, respectively. Homology and conserved domain searches were performed using the BLAST algorithm of NCBI. Sequence management and alignment were carried out using Vector NTI software (Invitrogen, Carlsbad, CA, USA). Alignment and phylogenetic analyses were performed using the AlignX module of Vector NTI.

GenBank Accession Numbers for udh Sequences

The udh gene sequence from *P. syringae* has been deposited with GenBank, Accession Number EU377538 (nucleic acid sequence is SEQ ID NO:1; amino acid sequence is SEQ ID NO:2). The corresponding genes from *A. tumefaciens* and *P. putida* were deposited with Accession Numbers BK006462 (DNA: SEQ ID NO:23; protein: SEQ ID NO:24) and BK006380 (DNA: SEQ ID NO:25; protein: SEQ ID NO:26), respectively.

Enzymatic Analysis of Udh Activities

Bacterial lysates for enzymatic analysis were prepared by the freeze-thaw method. *E. coli* strains harboring udh genes were grown overnight in LB medium containing 0.1 mM IPTG (Isopropyl β-D-1-thiogalactopyranoside). Pellets were re-suspended in 1 mg/mL lysozyme solution and incubated on ice for 30 min. The suspensions were frozen in liquid nitrogen then thawed in a 37° C. water bath. This step was repeated five times. Cell lysates were centrifuged at 14,000 rpm at 4° C. for 15 min, and the supernatant was used for enzymatic analysis. Udh activities on glucuronate were measured by monitoring NADH (nicotinamide adenine dinucleotide, reduced) generation at 340 nm (38). The reaction mixture was consisted of 2.5 mM glucuronate, 0.9 mM NAD$^+$ (nicotinamide adenine dinucleotide), and 100 mM sodium phosphate buffer. The reaction was initiated by the addition of lysate to the reaction mixture at room temperature, and monitored. For determination of the optimum pH for Udh activity, the reaction mixture was adjusted to pH 6.5 to 9.9 by the addition of HCl or NaOH solutions. The total protein concentration was determined using the Bradford method (Bradford (1976) Anal Biochem 72:248-54). Specific activities were indicated as units per milligram of total protein (1 U=1 μmol NADH generated/min). Chemicals were purchased from Sigma-Aldrich (St. Louis, Mo., USA).

Results

Cloning of udh Gene from *Pseudomonas syringae*

The screen established to identify the gene corresponding to Udh activity in *P. syringae* utilized a mutant strain of *E. coli* MG1655. A deletion of uxaC prevents growth on glucuronate while retaining the ability to grow on glucarate as a sole carbon source. Since Udh catalyzes the conversion of glucuronate to glucarate (3, 38), *E. coli* MG1655ΔuxcaC clones harboring udh genes from a *P. syringae* genomic library should grow on glucuronate as the sole carbon source. *E. coli* DH10B and pTrc99A were used as the host strain and plasmid vector, respectively, for initial construction of the *P. syringae* genomic library. A library plasmid pool was prepared from the *E. coli* DH10B clone pool, and then used to transform the ΔuxaC strain. Transformed ΔuxaC clones were incubated on M9 minimal agar containing glucuronate for 4 days at 30° C.

From ten agar plates, 28 clones were selected for further screening, each of which contained an inserted fragment of 2-5 kb. From these, 8 clones with different sized inserts were sequenced for comparison with the *P. syringae* genome sequence (GenBank Accession Number NC_004578). Six of these clones included iolE, iolB, or both of them, while one clone contained the unassigned PSPTO_1053 open reading frame. The final clone included a chimera of the iolEB and PSPTO_1053 regions. The open reading frames from the library fragments were PCR-amplified and inserted into expression vector pTrc99A, yielding plasmids pTiolE, pTiolB, pTiolEB and pT1053. Clones containing these vectors were used to determine which gene corresponded to uronate dehydrogenase activity. *E. coli* MG1655, the ΔuxaC derivative, and four ΔuxaC clones transformed with the candidate genes were incubated on M9 minimal agar containing glucuronate as the sole carbon source. Wild type, ΔuxaC (pTiolB), ΔuxaC (pTiolEB), and ΔuxaC (pT1053) strains grew on M9-glucuronate agar, while the ΔuxaC (pTrc99A) and ΔuxaC (pTiolE) strains did not. Therefore, iolB and PSPTO_1053 were responsible for growth on glucuronate as the sole carbon source, identifying them as candidate udh genes.

Figure 6:
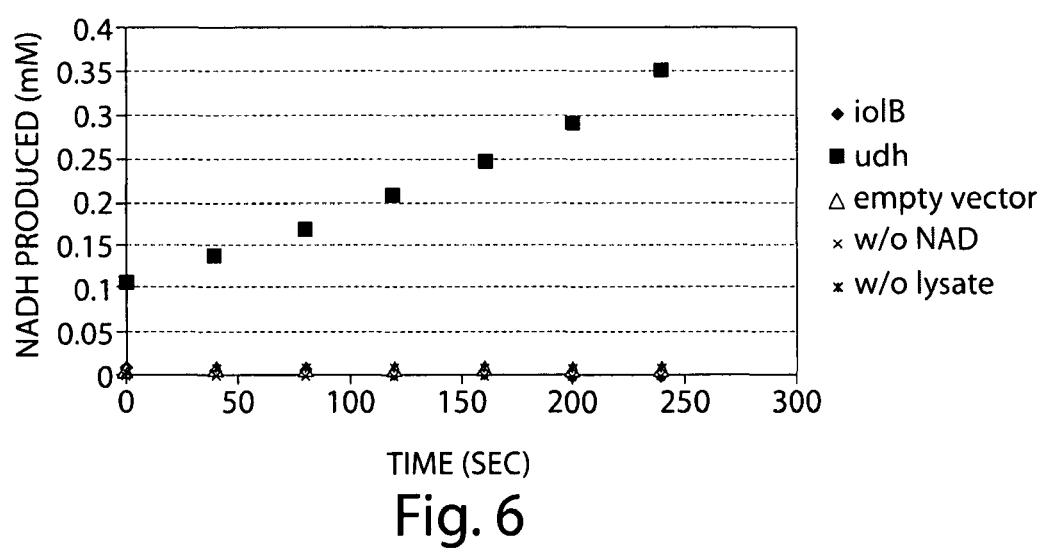
FIG. 6 is a graph depicting an enzymatic assay of putative Udh from P. syringae. E. coli lysates containing the expressed protein of the PSPTO_1053 ORF are capable of oxidizing glucuronic acid, which was supplied as the substrate, using NAD+ as a co-factor to produce glucaric acid as product. NADH production was measured to confirm the desired activity.

To further discriminate between the two candidate genes, plasmids pTiolB and pT1053were used to transform *E. coli* DH10B to express the recombinant genes. The resulting clones were grown in LB medium with 0.1 mM IPTG. Analysis of Udh activity in crude lysates from these two clones suggested that the strain harboring pT1053 exhibits Udh activity, but not pTiolB (FIG. 6). The assay employed glucuronate as a substrate and monitored production of NADH at 340 nm. Consequently, the 828 by PSPTO_1053 gene was deduced to encode uronate dehydrogenase. The gene is hereafter referred to as udh and was registered to Genbank (ncbi.nlm.nih.gov/Genbank/) as Accession Number EU377538 (nucleic acid sequence is SEQ ID NO:1; amino acid sequence is SEQ ID NO:2).

Cloning and Identification of udh Genes from *P. putida* and *A. tumefaciens*

Figure 7:
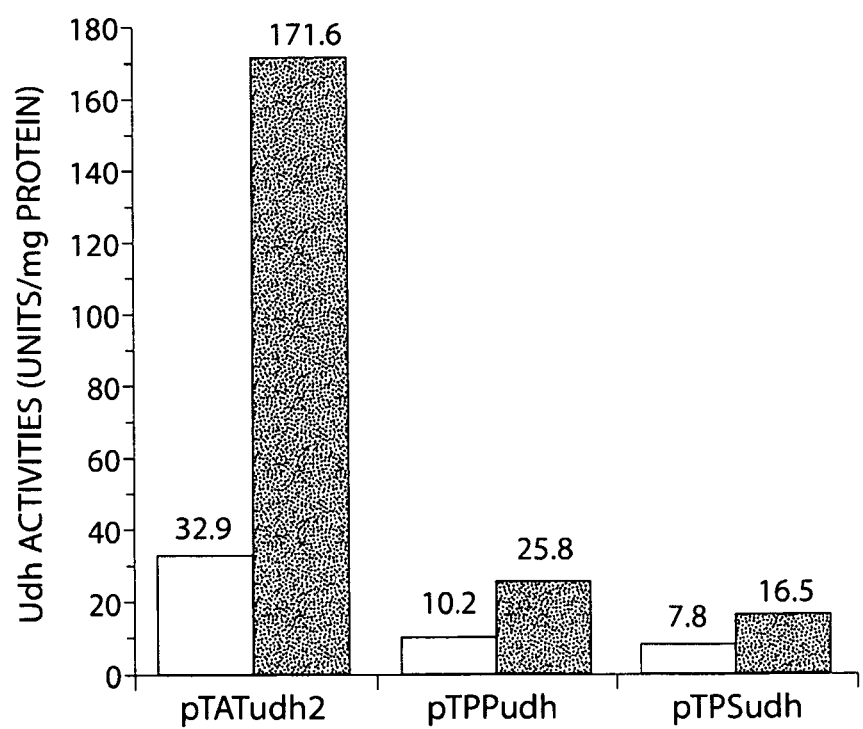
FIG. 7 is a graph showing activities of expressed udh genes from various sources in crude lysates of E. coli. pTATudh2 =Agrobacterium tumefaciens, pTPPudh =Pseudomonas putida, pTPSudh =Pseudomonas syringae. Glucuronic acid was supplied as the substrate, using NAD+ as a co-factor to produce glucaric acid as product. Open bars =without IPTG, Filled bars =with 0.1mM IPTG.

The translated protein sequence of udh from *P. syringae* was analyzed using BLASTP from NCBI (ncbi.nlm.nih.gov/blast/) to identify putative homologues. The Udh activity of *A. tumefaciens* has been studied previously (5, 6, 43). The translation of open reading frame Atu3143 of *A. tumefaciens* had the highest sequence identity of 47.8% and was considered a candidate for a homologous Udh. Another candidate open reading frame, PP1171 of *Pseudomonas putida* KT2440, was also found to have high similarity to *P. syringae* Udh, with a sequence identity of 75.6%. Atu3143 and PP1171 were PCR-amplified from their respective genomes and, along with udh from *P. syringae*, were integrated into plasmid vector pTrc99SE to create plasmids pTATudh2, pTPPudh, and pTPSudh, respectively, for comparison of relative activities of the expressed recombinant proteins. Transformed DH10B clones were cultivated in LB with or without 0.1 mM IPTG before preparing crude lysates to carry out enzymatic analysis (FIG. 7). These assays confirmed a NAD$^+$—consuming activity in the presence of glucuronate as a substrate for the recombinant proteins of *A. tumefaciens* and *P. putida*, similar to that previously obtained with *P. syringae*. The two udh genes from *A. tumefaciens* and *P. putida* were also deposited to Genbank as Accession Numbers BK006462 (DNA: SEQ ID NO:23; protein: SEQ ID NO:24) and BK006380 (DNA: SEQ ID NO:25; protein: SEQ ID NO:26), respectively.

Purification and Characterization of Recombinant Udh, and Analysis of the Reaction Product Enzyme reactions using crude *E. coli* lysates containing the *P. syringae* udh gene confirmed the presence of an activity that utilized glucuronate as a substrate, with the reaction rate proportional to glucuronate concentration for low substrate loads (data not shown). The activity also utilized NAD$^+$ but not NADP$^+$ as a co-factor (data not shown). These results indicated that the substrate was oxidized. An examination of the structure of glucuronate suggests two possible points of oxidation: the conversion of an alcohol to a ketone, or the conversion of the aldehyde to carboxylic acid, the latter reaction producing glucarate. The difference in these two products should be evident from a mass spectrum, as the former would result in a mass difference of −2 relative to the substrate, while the latter would produce a mass difference of +16. To confirm the product of the enzyme reaction as glucarate, a sample was analyzed by LC-MS. The spectra of the eluent separated from the enzyme reaction and a glucarate standard are in agreement, suggesting glucarate as the product of the Udh reaction (FIG. 8).

Figure 9:
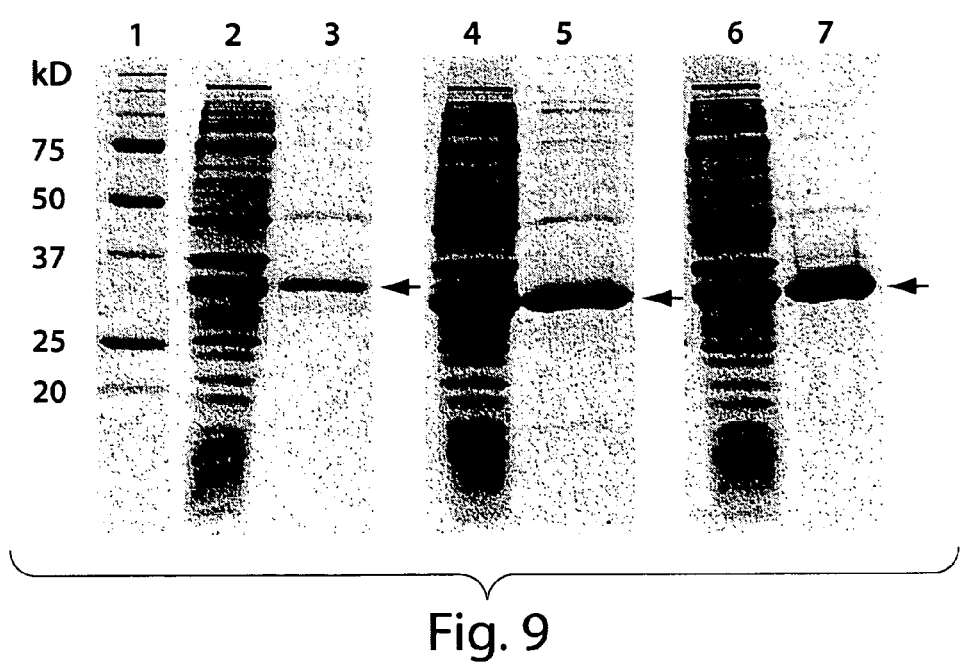
FIG. 9 depicts SDS-PAGE analysis of purified Udhs. The purified Udhs were subjected to electrophoresis in a 12% sodium dodecylsulfate polyacrylamide gel under denaturing conditions. Lane 1, molecular weight markers; lanes 2 and 3, crude extract and purified A. tumefaciens Udh of E. coli BL21(DE3) expressing pETATu; lanes 4 and 5, crude extract and purified P. putida Udh of E. coli BL21(DE3) expressing pETPPu; lanes 6 and 7, crude extract and purified P. syringae Udh of E. coli BL21(DE3) expressing pETPSu. The purified Udhs are indicated by the arrow symbols.

Each of the three udh genes were expressed in *E. coli* with 6×-His tags and purified to determine the kinetic parameters of the corresponding enzymes. Purified enzymes were analyzed by SDS-PAGE to confirm molecular weight of the monomer and estimate purity (FIG. 9). The Udh of *P. syringae* and *P. putida* were both approximately 30 KDa molecular weight, which is consistent both with the translation of the cloned gene and previous reports (38). The *A. tumefaciens* Udh is slightly larger, at 32 KDa. The purified preparations were used to determine the kinetic parameters, $k_{cat}$ and $K_m$, for each of the enzymes. Both glucuronate and galacturonate were used as substrates, and NAD$^+$ co-factor concentration was also varied to determine the corresponding $K_m$ (Table 5). Measurements of $k_{cat}$ obtained by varying co-factor concentration were within 20% of the values obtained using glucuronate as the substrate (data not shown). In all cases, $k_{cat}$ was higher for glucuronate than for galacturonate. The highest rate constant was found for the A. tumefaciens enzyme utilizing glucuronate as substrate ($k_{cat}=1.9\times10^2$ s$^{-1}$), which was more than 2-fold higher than the rate for the Pseudomonas enzymes. However, the Michaelis (affinity) constant was lower for galacturonate in all cases, with the lowest $K_m$, 0.04 mM, found for the P. syringae enzyme utilizing galacturonate as substrate. The first order rate constants, $k_{cat}/K_m$, are highest for galacturonate as substrate, with the largest difference between glucuronate and galacturonate observed for P. syringae.

Figure 10A:
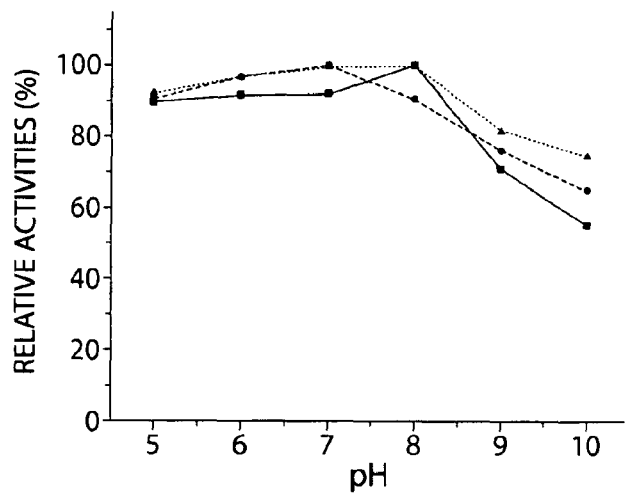
FIG. 10a shows relative activities as a function of pH.

The responses of the enzyme activities to changes in pH and temperature were also investigated (FIG. 10). A pH optimum of 8.0 was observed for both the A. tumefaciens and P. syringae enzymes, although the activity was relatively unchanged between pH~7 and pH~8 for P. syringae Udh (FIG. 10a). This pH behavior is consistent with previous reports for P. syringae Udh (3). The P. putida enzyme exhibited highest activity at pH~7.0. In general, enzyme activities varied approximately 10% between pH~5 and pH~8, with significant drops in activity observed for pH values greater than 8 for all three enzymes.

Figure 10B:
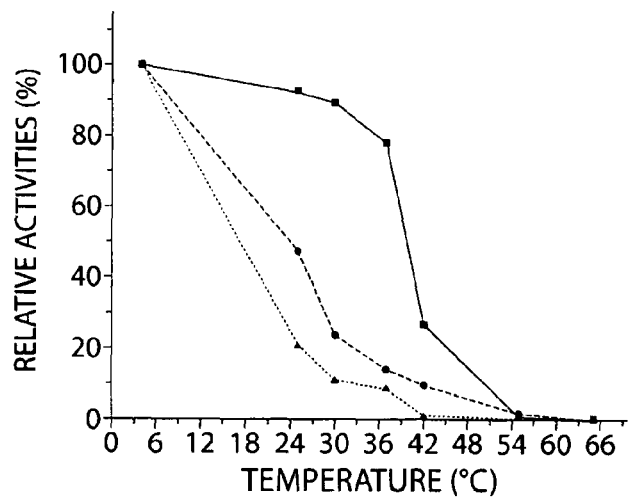
FIG. 10b shows relative activities after incubation for 30 minutes at indicated temperatures.
Figure 10C:
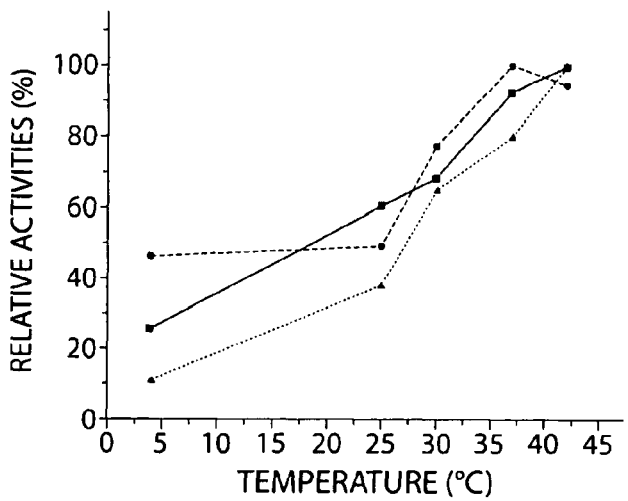
FIG. 10c shows relative activities as a function of assay temperature. Glucuronic acid was supplied as the substrate, using NAD+ as a co-factor to produce glucaric acid as product. Square with plain line: A. tumefaciens Udh. Circle with dashed line: P. putida Udh. Triangle with dotted line: P. syringae Udh.

The impact of temperature was evaluated in two ways. First, the thermal stability was examined by exposing enzyme preparations to various temperatures for 30 minutes, then performing the enzyme assay under standard conditions. The A. tumefaciens Udh was found to exhibit a significantly higher thermal stability than either of the Pseudomonas enzymes (FIG. 10b). The activity remained near 80% of maximum after exposure of the A. tumefaciens preparation to 37° C., while the corresponding activities for both of the other enzymes was below 20% of maximum. The stability profiles for both Pseudomonas enzymes were similar to one another. Finally, enzyme activity was evaluated for assays conducted under increasing temperatures. These activities followed a general trend of increasing activity with increasing temperature between 4 and 42° C., which is consistent with an Arrhenius-type dependence of the catalytic rate constant on temperature (FIG. 10c).

For final characterization of the products of these reactions, the boronic acid affinity gel was used to isolate the putative glucarate produced from all three enzymes in in vitro reactions using purified proteins. Samples of the three products were then subjected to circular dichroism (CD) analysis to examine the stereochemistry of the compounds. All three spectra were in agreement with a glucarate standard, confirming the identity of the product as glucaric acid and the identity of the three genes as those encoding uronate dehydrogenases (data not shown).

Discussion

Uronate dehydrogenase (Udh) catalyzes the first step of an oxidation pathway for aldohexuronate catabolism in bacteria. In bacteria, only limited studies of Udh in P. syringae and A. tumefaciens have been reported. Moreover, Udh has been even more rarely studied in eukaryotes. A Udh sequence was reported in the wine grape Vitis vinifera, where it was identified as galacturonate reductase (EC 1.1.1.203; BRENDA Accession Number A 1Y2Z0, GenBank Accession Number DQ843600). We synthesized this gene with codon usage optimized for expression in E. coli (DNA 2.0, Menlo Park, Calif.), and expressed the recombinant protein. However, no activity related to Udh was observed when using either NAD$^+$ or NADP$^+$ as a cofactor (data not shown). An alignment of this sequence with the P. syringae Udh identified in the current work reveals only 10% identity between them. We can not rule out the possibility that the V. vinifera enzyme could not be functionally expressed in E. coli; however, based on the alignment, we conclude that the reported sequence from V. vinifera is either not uronate dehydrogenase, or it is a highly divergent version of the enzyme.

A shotgun library of P. syringae was introduced into E. coli ΔuxaC to screen for the udh gene encoding uronate dehydrogenase, and PSPTO_1053 and iolB gene were identified and screened as possible Udh candidates. By enzymatic analysis, PSPTO_1053 was ultimately identified to be the udh gene encoding uronate dehydrogenase. In a uxaC deletion mutant of E. coli, where glucuronate catabolism is abolished, glucuronate was converted to glucarate by uronate dehydrogenase, then degraded to pyruvate or 2-phosphoglycerate from which it can be used as an energy source (27, 33). In E. coli ΔuxaC, introduction of the iolB gene allowed for growth on M9 agar containing glucuronate as a sole carbon source as well, but this gene did not possess Udh activity. IolB has previously been reported as a protein related to myo-inositol catabolism in Bacillus subtilis and Lactobacillus casei (41, 42). IolB belongs to the iol operon used for myo-inositol degradation in Bacillus subtilis and converts 5-deoxy-glucuronate to 2-deoxy-5-keto-D-gluconate (42). IolB of P. syringae has about 48% homology with that of B. subtilis. The precise mechanism of glucuronate consumption in cells harboring IolB in our screen is unclear. Presumably, this protein is able to convert glucuronate to an analogous compound that is compatible with E. coli metabolism.

Figure 11A:
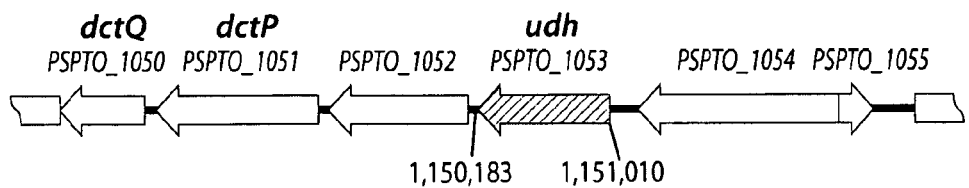
FIG. 11a: P. syringae pv. tomato str. DC3000.
Figure 11B:
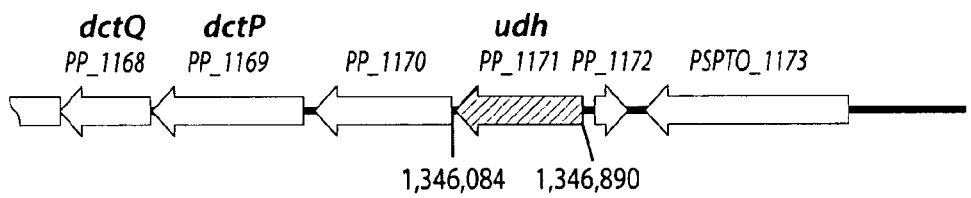
FIG. 11b: P. putida KT2440.
Figure 11C:
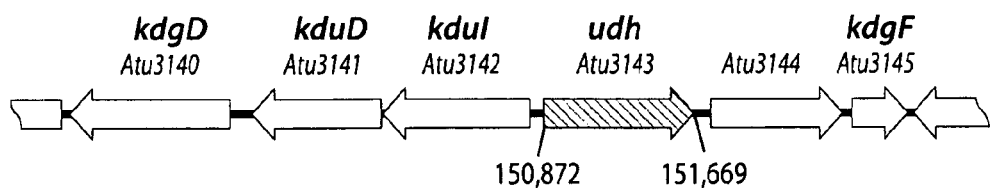
FIG. 11c: A. tumefaciens str. C58.

The udh gene loci in the genomes of P. syringae, P. putida, and A. tumefaciens are shown in FIG. 11. The udh loci of P. syringae and P. putida are at about 1,150 and 1,346 kbp, respectively, while the udh locus in A. tumefaciens is at about 150 kbp. In A. tumefaciens, the genes, Atu3140, 3141, 3142, and 3145 adjacent to udh are kdgD, kduD, kduI, and kdgF, respectively, and are related to pectin degradation. Pectin is a heteropolysaccharide, consisting of α-1,4-linked D-galacturonate residues, which is derived from plant cell walls. Pectin degradation and uptake by bacteria has been well-researched in phytopathogenic Pectobacterium including Erwinia chrysanthemi and Erwinia carotovora by Hugouvieux-Cotte-Pattat et al. (12-14). In E. chrysanthemi, pectin is degraded by genes of the kdu or kdg operon to use as an energy source. In P. syringae and P. putida, the genes adjacent to udh are identified as TRAP (Tripartite ATP-independent periplasmic) dicarboxylate transporters and porin. Among these genes, the porin protein (PSPTO_1054, PP_1173) is known to be related to uptake of oligogalacturonate derived from pectin degradation (34). Uronate dehydrogenase in plant pathogenic bacteria might therefore function in the utilization of a hexuronate, derived from host plant cell wall pectin, which is subsequently converted to hexarate.

Figure 12A:
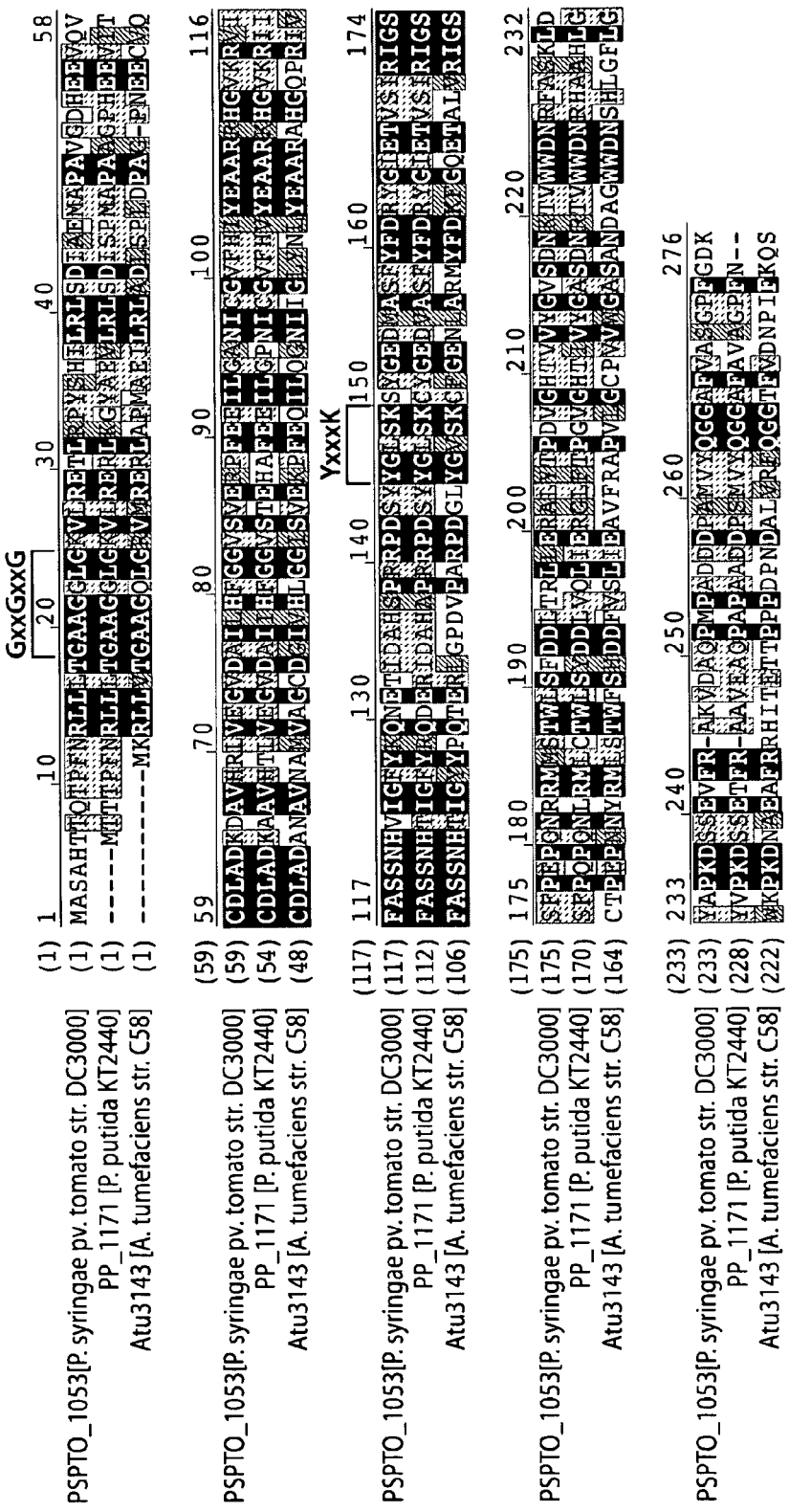
FIG. 12a depicts an alignment of uronate dehydrogenase from P. syringae pv. tomato str. DC3000 (SEQ ID NO:2), P. putidaKT2440 (SEQ ID NO:26), and A. tumefaciens str. C58 (SEQ ID NO:24). For alignment, identical, conservative, and similar amino acid sequences are represented as black, dark grey, and light grey blocks, respectively. Primary sequence motifs are indicated as GxxGxxG and YxxxK.
Figure 12B:
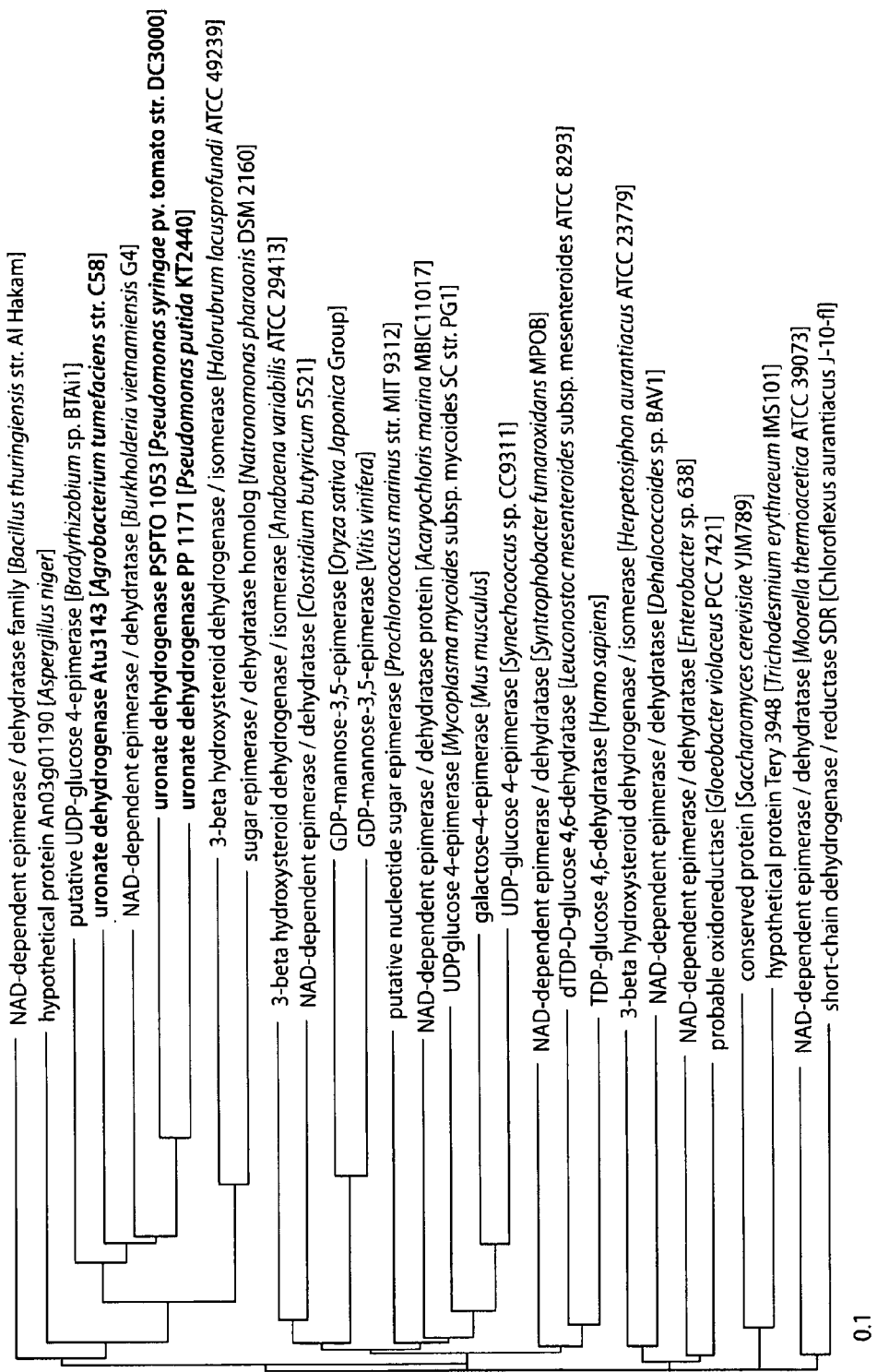
FIG. 12b depicts phylogenetic analysis of the uronate dehydrogenase homologues from diverse prokaryotic and eukaryotic species. Phylogenetic analysis was performed using homologues of PSPTO_1053 of P. syringae pv. tomato str. DC3000. Uronate dehydrogenases are indicated in bold.

Alignment of the three uronate dehydrogenases from P. syringae, P. putida, and A. tumefaciens and phylogenetic analysis of their homologs were performed (FIG. 12). The sequences of the enzymes show two primary sequence motifs, YxxxK and GxxGxxG, related to conserved domains (FIG. 12a). The YxxxK motif is located between Tyr$_{145}$ and Lys$_{149}$ of P. syringae Udh, and is the primary motif of the 3-alpha/beta hydroxysteroid dehydrogenase domain (11, 37). The GxxGxxG motif located in Gly$_{18-24}$ of P. syringae Udh is similar to Rossman folds, GxxxG or Gx$_{1-2}$GxxG, which have been discovered in NAD$^+$ binding domains (20). In the phylogenetic analysis, the uronate dehydrogenase shows homologies with NAD-dependent epimerase/dehydratase, nucleotide sugar epimerase, 3-beta hydroxysteroid dehydrogenase/isomerase, and short-chain dehydrogenase/reductase in archaea and bacteria including proteobacteria, cyanobacteria, green nonsulfur bacteria, and gram-positive bacteria, as well as homology with nucleotide sugar epimerase in a few eukaryotes including fungi, plants, and human (FIG. 12b). The three uronate dehydrogenases screened in this study are present in alpha and gamma-proteobacteria, and their homologies are relatively close to the Archaea, *Halorubrum lacusprofundi* and *Natronomonas pharaonis*, and the fungus, *Aspergillus niger*.

We have screened and sequenced three uronate dehydrogenases from *A. tumefaciens, P. putida*, and *P. syringae*, which can effectively convert glucuronate to glucarate. While this enzyme is important for the catabolism of uronic acids in several types of bacteria, it may also be useful in the development of biosynthetic pathways for the production of aldaric acids, such as glucaric acid. Glucarate is the end-product of nucleotide sugar metabolism and is found naturally in mammals and plant (21, 39). Glucarate and its derivatives such as glucaro-1,4-lactone have been studied previously as detoxifying and natural anti-carcinogenic compounds (8, 21, 36, 39), as well as a building block for polymer synthesis (16). It has also been designated as a potential "top value-added" chemical to be produced from biomass (40). Presently, glucarate is synthesized from glucose by chemical oxidation using a strong oxidant such as nitric acid or nitric oxide (25). We have used the udh of *P. syringae* identified in this study to successfully produce glucaric acid from a synthetic pathway in *E. coli* (26).

References for Example 2
1. Amann, E., B. Ochs, and K. J. Abel. 1988. Tightly regulated tac promoter vectors useful for the expression of unfused and fused proteins in *Escherichia coli*. Gene 69:301-315.
2. Ashwell, A., A. J. Wahba, and J. Hickman. 1958. A new pathway of uronic acid metabolism. Biochim Biophys Acta 30:186-187.
3. Bateman, D. F., T. Kosuge, and W. W. Kilgore. 1970. Purification and properties of uronate dehydrogenase from *Pseudomonas syringae*. Arch Biochem Biophys 136:97-105.
4. Buell, C. R., V. Joardar, M. Lindeberg, J. Selengut, I. T. Paulsen, M. L. Gwinn, R. J. Dodson, R. T. Deboy, A. S. Durkin, J. F. Kolonay, R. Madupu, S. Daugherty, L. Brinkac, M. J. Beanan, D. H. Haft, W. C. Nelson, T. Davidsen, N. Zafar, L. Zhou, J. Liu, Q. Yuan, H. Khouri, N. Fedorova, B. Tran, D. Russell, K. Berry, T. Utterback, S. E. Van Aken, T. V. Feldblyum, M. D'Ascenzo, W. L. Deng, A. R. Ramos, J. R. Alfano, S. Cartinhour, A. K. Chatterjee, T. P. Delaney, S. G. Lazarowitz, G. B. Martin, D. J. Schneider, X. Tang, C. L. Bender, O. White, C. M. Fraser, and A. Collmer. 2003. The complete genome sequence of the *Arabidopsis* and tomato pathogen *Pseudomonas syringae* pv. tomato DC3000. Proc Natl Acad Sci USA 100:10181-10186.
5. Chang, Y. F., and D. S. Feingold. 1970. D-glucaric acid and galactaric acid catabolism by *Agrobacterium tumefaciens*. J Bacteriol 102:85-96.
6. Chang, Y. F., and D. S. Feingold. 1969. Hexuronic acid dehydrogenase of *Agrobacterium tumefaciens*. J Bacteriol 99:667-673.
7. Cynkin, M. A., and G. Ashwell. 1960. Uronic acid metabolism in bacteria. IV. Purification and properties of 2-keto-3-deoxy-D-gluconokinase in *Escherichia coli*. J Biol Chem 235:1576-1579.
8. Duff, K. 2002. Calcium-D-glucarate. Altern Med Rev 7:336-339.
9. Farmer, J. J., 3rd, and R. G. Eagon. 1969. Aldohexuronic acid catabolism by a soil *Aeromonas*. J Bacteriol 97:97-106.
10. Goodner, B., G. Hinkle, S. Gattung, N. Miller, M. Blanchard, B. Qurollo, B. S. Goldman, Y. Cao, M. Askenazi, C. Halling, L. Mullin, K. Houmiel, J. Gordon, M. Vaudin, O. Iartchouk, A. Epp, F. Liu, C. Wollam, M. Allinger, D. Doughty, C. Scott, C. Lappas, B. Markelz, C. Flanagan, C. Crowell, J. Gurson, C. Lomo, C. Sear, G. Strub, C. Cielo, and S. Slater. 2001. Genome sequence of the plant pathogen and biotechnology agent *Agrobacterium tumefaciens* C58. Science 294:2323-2328.
11. Hoffmann, F., C. Sotriffer, A. Evers, G. Xiong, and E. Maser. 2007. Understanding oligomerization in 3alpha-hydroxysteroid dehydrogenase/carbonyl reductase from *Comamonas testosteroni*: an in silico approach and evidence for an active protein. J Biotechnol 129:131-139.
12. Hugouvieux-Cotte-Pattat, N., G. Condemine, W. Nasser, and S. Reverchon. 1996. Regulation of pectinolysis in *Erwinia chrysanthemi*. Annu Rev Microbiol 50:213-257.
13. Hugouvieux-Cotte-Pattat, N., W. Nasser, and J. Robert-Baudouy. 1994. Molecular characterization of the *Erwinia chrysanthemi* kdgK gene involved in pectin degradation. J Bacteriol 176:2386-2392.
14. Hugouvieux-Cotte-Pattat, N., and S. Reverchon. 2001. Two transporters, TogT and TogMNAB, are responsible for oligogalacturonide uptake in *Erwinia chrysanthemi* 3937. Mol Microbiol 41:1125-1132.
15. Hugouvieux-Cotte-Pattat, N., and J. Robert-Baudouy. 1987. Hexuronate catabolism in *Erwinia chrysanthemi*. J Bacteriol 169:1223-1231.
16. Ibert, M., F. Marsais, N. Merbouh, and C. Bruckner. 2002. Determination of the side-products formed during the nitroxide-mediated bleach oxidation of glucose to glucaric acid. Carbohydr Res 337:1059-1063.
17. Kang, Y., T. Durfee, J. D. Glasner, Y. Qiu, D. Frisch, K. M. Winterberg, and F. R. Blattner. 2004. Systematic mutagenesis of the *Escherichia coli* genome. J Bacteriol 186:4921-4930.
18. Kilgore, W. W., and M. P. Starr. 1959. Catabolism of galacturonic and glucuronic acids by *Erwinia carotovora*. J Biol Chem 234:2227-2235.
19. Kilgore, W. W., and M. P. Starr. 1959. Uronate oxidation by phytopathogenic pseudomonads. Nature 183:1412-1413.
20. Kleiger, G., and D. Eisenberg. 2002. GXXXG and GXXXA motifs stabilize FAD and NAD(P)-binding Rossmann folds through C(alpha)-H, O hydrogen bonds and van der waals interactions. J Mol Biol 323:69-76.
21. Marsh, C. A. 1986. Biosynthesis of D-glucaric acid in mammals: a free-radical mechanism? Carbohydr Res 153:119-131.
22. Mata-Gilsinger, M., and P. Ritzenthaler. 1983. Physical mapping of the exuT and uxaC operators by use of exu plasmids and generation of deletion mutants in vitro. J Bacteriol 155:973-982.
23. Mc, R. R., and G. D. Novelli. 1958. Glucuronate metabolism by *Aerobacter aerogenes*. Nature 182:1504-1505.
24. Mc, R. R., A. K. Williams, and W. J. Payne. 1959. Alduronic acid metabolism by bacteria. J Bacteriol 77:212-216.
25. Merbouh, N., J. Francois Thaburet, M. Ibert, F. Marsais, and J. M. Bobbitt. 2001. Facile nitroxide-mediated oxidations of D-glucose to D-glucaric acid. Carbohydr Res 336:75-78.
26. Moon, T. S., S. H. Yoon, A. M. Lanza, J. D. Roy-Mayhew, and K. J. Prather. 2008. Production of Glucaric Acid from a Synthetic Pathway in Recombinant *Escherichia coli*. Appl Environ Microbiol.

27. Neidhardt, F. C., and R. Curtiss. 1996. *Escherichia coli* and *Salmonella*: cellular and molecular biology, 2nd ed. ASM Press, Washington, D.C.
28. Payne, W. J., and R. R. Mc. 1958. Glucuronate isomerase from *Serratia marcescens*. Biochim Biophys Acta 29:466-467.
29. Poon, R., D. C. Villeneuve, I. Chu, and R. Kinach. 1993. HPLC determination of D-glucaric acid in human urine. J Anal Toxicol 17:146-150.
30. Portalier, R. C., J. M. Robert-Baudouy, and G. M. Nemoz. 1974. [Studies of mutations in the uronic isomerase and altronic oxidoreductase structural genes of *Escherichia coli* K 12 (author's transl)]. Mol Gen Genet. 128:301-319.
31. Robert-Baudouy, J., J. Jimeno-Abendano, and F. Stoeber. 1982. D-Mannonate and D-altronate dehydratases of *Escherichia coli* $K_{12}$. Methods Enzymol 90 Pt E:288-294.
32. Robert-Baudouy, J. M., and F. R. Stoeber. 1973. [Purification and properties of D-mannonate hydrolyase from *Escherichia coli* K12]. Biochim Biophys Acta 309:473-485.
33. Roberton, A. M., P. A. Sullivan, M. C. Jones-Mortimer, and H. L. Kornberg. 1980. Two genes affecting glucarate utilization in *Escherichia coli* K12. J Gen Microbiol 117:377-382.
34. Rodionov, D. A., M. S. Gelfand, and N. Hugouvieux-Cotte-Pattat. 2004. Comparative genomics of the KdgR regulon in *Erwinia chrysanthemi* 3937 and other gamma-proteobacteria. Microbiology 150:3571-3590.
35. Sambrook, J., and D. W. Russell. 2001. Molecular cloning: a laboratory manual, 3rd ed. Cold Spring Harbor Laboratory Press, Cold Spring Harbor, N.Y.
36. Singh, J., and K. P. Gupta. 2003. Calcium glucarate prevents tumor formation in mouse skin. Biomed Environ Sci 16:9-16.
37. Thomas, J. L., J. I. Mason, S. Brandt, B. R. Spencer, Jr., and W. Norris. 2002. Structure/function relationships responsible for the kinetic differences between human type 1 and type 2 3 beta-hydroxysteroid dehydrogenase and for the catalysis of the type 1 activity. J Biol Chem 277:42795-42801.
38. Wagner, G., and S. Hollmann. 1976. Uronic acid dehydrogenase from *Pseudomonas syringae*. Purification and properties. Eur J Biochem 61:589-596.
39. Walaszek, Z. 1990. Potential use of D-glucaric acid derivatives in cancer prevention. Cancer Lett 54:1-8.
40. Werpy, T. A., and G. Petersen. 2004. Top value added chemicals from biomass, vol. 1. PNNL and NREL.
41. Yebra, M. J., M. Zuniga, S. Beaufils, G. Perez-Martinez, J. Deutscher, and V. Monedero. 2007. Identification of a gene cluster enabling *Lactobacillus casei* BL23 to utilize myo-inositol. Appl Environ Microbiol 73:3850-3858.
42. Yoshida, K., M. Yamaguchi, T. Morinaga, M. Kinehara, M. Ikeuchi, H. Ashida, and Y. Fujita. 2008. myo-Inositol Catabolism in *Bacillus subtilis*. J Biol Chem 283:10415-10424.
43. Zajic, J. E. 1959. Hexuronic dehydrogenase of *Agrobacterium tumefaciens*. J Bacteriol 78:734-735.

TABLE 4

Strains, plasmids, and primers used in this study.

| Plasmids and Primers | Description | Reference or source |
|---|---|---|
| Strains | | |
| *Pseudomonas syringae* pv. tomato strain DC3000 | Wild type | |
| *Pseudomonas putida* KT2440 | Wild type | (ATCC 47504) |
| *Escherichia coli* DH10B | F-mcrA Δ(mrr-hsdRMS-mcrBC) φ80lacZΔM15 ΔlacX74 recA1 endA1 araD139 Δ(ara, leu) 7697 galU galK λ⁻ rpsL nupG | (Invitrogen Corp., Carlsbad, CA, USA) |
| *Escherichia coli* MG1655 Δ uxaC | Wild type with deletion of uxaC gene encoding D-glucuronate isomerase | (17) |
| *Escherichia coli* BL21 (DE3) | F-ompT hsdS$_B$ (r$_B^-$ m$_B^-$) gal dcm (DE3) | (Invitrogen Corp., Carlsbad, CA, USA) |
| Plasmids | | |
| pBluescriptII | lac promoter, ColE1 origin, Ampicillin resistance, lacZ | (Stratagene, La Jolla, CA, USA) |
| pTrc99A | trc promoter, pBR322 origin, Ampicillin resistance, lacI$^q$ | (1) |
| pET21b | T7 promoter, ColE1 origin, Ampicillin resistance, lacI | (Novagen, Darmstadt, Germany) |
| pTrc99SE | pTrc99 containing RBS sequence of AGGAGGTAATAAAT (SEQ ID NO: 5) | (Seon-Won, Kim) |
| pTiolE | pTrc99A with iolE of *P. syringae* | This study |

TABLE 4-continued

Strains, plasmids, and primers used in this study.

| Plasmids and Primers | Description | Reference or source |
|---|---|---|
| pTiolB | pTrc99A with iolB of *P. syringae* | This study |
| pTiolEB | pTrc99A with iolE and iolB of *P. syringae* | This study |
| pT1053 | pTrc99A with PSPTO_1053 of *P. syringae* | This study |
| pTepi | pTrc99A with epi; udh (PSPTO 1053) of *P. syringae* | This study |
| pTATudh2 | pTrc99SE with udh of *A. tumefaciens* | This study |
| pTPPudh | pTrc99SE with udh of *P. putida* | This study |
| pTPSudh | pTrc99SE with udh of *P. syringae* | This study |
| pETATu | pET21b with udh of *A. tumefaciens* | This study |
| pETPPu | pET21b with udh of *P. putida* | This study |
| pETPSu | pET21b with udh of *P. syringae* | This study |

Primers [a]

| | | |
|---|---|---|
| iolE-F | 5'-CGAATTCAGGAGGTACAACCATGCCTGTTTCAG-3' (SEQ ID NO: 6) | |
| iolE-R | 5'-CGTCGACTTATCGCGCATCGGCCAGCAGTTG-3' (SEQ ID NO: 7) | |
| iolB-F | 5'-CGAATTCAGGAGGATTGAATCATGAGTC-3' (SEQ ID NO: 8) | |
| iolB-R | 5'-CGTCGACTTAAAGATCCAGCAGCCAGC-3' (SEQ ID NO: 9) | |
| 1053-F | 5'-GCCATGGCATCGGCTCATACCAC-3' (SEQ ID NO: 10) | |
| 1053-R | 5'-CGAGCTCTTATTTATCGCCGAACGGTCC-3' (SEQ ID NO: 11) | |
| ATudh2-F | 5'-CTAGAATTCATGAAACGGCTTCTTGTTACC-3' (SEQ ID NO: 12) | |
| ATudh-R | 5'-CTAGAGCTCTTAGCTCTGTTTGAAGATCGGGTTG-3' (SEQ ID NO: 13) | |
| PPudh-F | 5'-GTCGAATTCATGACCACTACCCCCTTCAATC-3' (SEQ ID NO: 14) | |
| PPudh-R | 5'-CTAGAGCTCCGTGGGGTTAGTTGAACGGGC-3' (SEQ ID NO: 15) | |
| PSudh-F | 5'-CTAGAATTCATGGCATCGGCTCATACCACTC-3' (SEQ ID NO: 16) | |
| ATuEQ-F | 5'-TCAGAGCTCGAAACGGCTTCTTGTTACCGGTGC-3' (SEQ ID NO: 17) | |
| ATuEQ-R | 5'-CTGAAGCTTGCTCTGTTTGAAGATCGGGTTGTCG-3' (SEQ ID NO: 18) | |
| PPuEQ-F | 5'-TCAGAGCTCGACCACTACCCCCTTCAATCGCC-3' (SEQ ID NO: 19) | |
| PPuEQ-R | 5'-CTGAAGCTTGTTGAACGGGCCGGCCACGGCG-3' (SEQ ID NO: 20) | |
| PSuEQ-F | 5'-TCAGAGCTCGGCATCGGCTCATACCACTCAAACTCC-3' (SEQ ID NO: 21) | |
| PSuEQ-R | 5'-CTGAAGCTTTTTATCGCCGAACGGTCCGGACGC-3' (SEQ ID NO: 22) | |

[a] Primer binding sites, restriction sites, start or stop codons were indicated as bold letters, double and single underlines, respectively.

TABLE 5

Turnover numbers ($k_{cat}$) and Michaelis constants ($K_m$) of uronate dehydrogenases from *A. tumefaciens*, *P. putida*, and *P. syringae*.

| | A. tumefaciens | | P. putida | | P. syringae | |
|---|---|---|---|---|---|---|
| | Glucuronate | Galacturonate | Glucuronate | Galacturonate | Glucuronate | Galacturonate |
| $k_{cat}$ (1/s) | 193.90 ± 11.84 | 91.85 ± 14.26 | 54.57 ± 2.60 | 30.08 ± 3.12 | 73.77 ± 3.13 | 24.02 ± 0.73 |
| $K_m$ (mM) | 0.37 ± 0.12 | 0.16 ± 0.12 | 0.25 ± 0.07 | 0.10 ± 0.06 | 0.28 ± 0.07 | 0.04 ± 0.01 |
| $k_{cat}/K_m$ | 524.05 | 574.06 | 218.28 | 300.80 | 263.46 | 600.50 |
| $k_{cat}$ (1/s) | 194 ± 12 | 92 ± 14 | 55 ± 3 | 30 ± 3 | 74 ± 3 | 24 ± 1 |
| $K_m$ (mM) | 0.37 ± 0.12 | 0.16 ± 0.12 | 0.25 ± 0.07 | 0.10 ± 0.06 | 0.28 ± 0.07 | 0.04 ± 0.01 |
| $k_{cat}/K_m$ | 524 | 574 | 218 | 301 | 263 | 601 |
| $k_{cat}$ ($10^2 \cdot$ 1/s) | 1.9 ± 0.12 | 0.9 ± 0.14 | 0.5 ± 0.03 | 0.3 ± 0.03 | 0.7 ± 0.03 | 0.2 ± 0.01 |
| $K_m$ (mM) | 0.37 ± 0.12 | 0.16 ± 0.12 | 0.25 ± 0.07 | 0.10 ± 0.06 | 0.28 ± 0.07 | 0.04 ± 0.01 |
| $10^2 \cdot k_{cat}/K_m$ | 5.2 | 5.7 | 2.2 | 3.0 | 2.6 | 6.0 |

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

We claim:

1. An isolated cell that recombinantly expresses a protein comprising the polypeptide set forth by SEQ ID NO: 2, 24, or 26, or a polypeptide that has least 95% identity to SEQ ID NO: 2, 24, or 26, wherein the polypeptide has uronate dehydrogenase activity, and wherein the cell produces glucaric acid.

2. The isolated cell of claim 1 wherein the uronate dehydrogenase is a bacterial uronate dehydrogenase, optionally a Pseudomonas syringae uronate dehydrogenase, a Pseudomonas putida uronate dehydrogenase or an Agrobacterium tumefaciens uronate dehydrogenase.

3. The isolated cell of claim 1 wherein the cell expresses a mammalian myo-inositol oxygenase, optionally a mouse myo-inositol oxygenase.

4. The isolated cell of claim 1 wherein the cell expresses a fungal or yeast myo-inositol 1-phosphate synthase.

5. The isolated cell of claim 4 wherein the myo-inositol 1-phosphate synthase is a Saccharomyces cerevisiae myo-inositol 1- phosphate synthase.

6. The isolated cell of claim 1, wherein the cell is a prokaryotic cell.

7. The isolated cell of claim 6 wherein the cell is a bacterial cell, optionally an *E. coli* cell.

8. The isolated cell of claim 3 or 4 wherein nucleic acids encoding the myo-inositol oxygenase or the myo-inositol 1-phosphate synthase have been modified by codon optimization for expression in bacteria.

9. The isolated cell of claim 1, wherein the cell is a eukaryotic cell.

10. The isolated cell of claim 9 wherein the cell is a fungal cell, a yeast cell, an insect cell, a plant cell, or a mammalian cell.

11. The isolated cell of claim 3 or 4 wherein the nucleic acids encoding the uronate dehydrogenase, myo-inositol oxygenase and/or myo-inositol 1-phosphate synthase are expressed on plasmids or are integrated into the genome of the cell.

12. The isolated cell of claim 3 or 4 wherein the production of glucaric acid is increased by recombinant expression of the uronate dehydrogenase, myo-inositol oxygenase and/or myo-inositol 1-phosphate synthase enzymes in the cell.

13. A method for producing glucaric acid comprising culturing the isolated cell of claim 1 to produce glucaric acid, optionally further comprising recovering the glucaric acid from the cells.

14. An isolated microorganism that recombinantly expresses a protein comprising the polypeptide set forth by SEQ ID NO: 2, 24, or 26, or a polypeptide that has least 95% identity to SEQ ID NO: 2, 24, or 26, wherein the polypeptide has uronate dehydrogenase activity, and wherein the microorganism produces glucaric acid.

15. The method of claim 13 wherein the uronate dehydrogenase is a bacterial uronate dehydrogenase, optionally a Pseudomonas syringae uronate dehydrogenase, a Pseudomonas putida uronate dehydrogenase or an Agrobacterium tumefaciens uronate dehydrogenase.

16. The method of claim 13 wherein the isolated cell expresses a mammalian myo-inositol oxygenase, optionally a mouse myo-inositol oxygenase.

17. The method of claim 13 wherein the isolated cell expresses a fungal or yeast myo-inositol 1-phosphate synthase, optionally a Saccharomyces cerevisiae myo-inositol 1-phosphate synthase.

18. The method of claim 13, wherein the cell is a prokaryotic cell.

19. The method of claim 18 wherein the cell is a bacterial cell, optionally an *E. coli* cell.

20. The method of claim 16 or 17 wherein nucleic acids encoding the myo-inositol oxygenase or myo-inositol 1-phosphate synthase have been modified by codon optimization for expression in bacteria.

21. The method of claim 13, wherein the cell is a eukaryotic cell, optionally a fungal cell, a yeast cell, an insect cell, a plant cell or a mammalian cell.

22. The method of claim 16 or 17 wherein the nucleic acids encoding the uronate dehydrogenase, myo-inositol oxygenase and/or myo-inositol 1-phosphate synthase are expressed on plasmids or are integrated into the genome of the cell.

23. The method of claim 16 or 17 wherein the production of glucaric acid is increased by recombinant expression of the uronate dehydrogenase, myo-inositol oxygenase and/or myo-inositol 1-phosphate synthase enzymes in the cell.

24. A recombinant expression vector comprising a transcription regulatory element linked to an isolated nucleic acid molecule selected from the group consisting of:
   (a) an isolated nucleic acid molecule comprising SEQ ID NO: 1, SEQ ID NO:23, or SEQ ID NO:25;
   (b) an isolated nucleic acid molecule encoding an amino acid sequence comprising the sequence of SEQ ID NO:2, SEQ ID NO:24 or SEQ ID NO:26;
   (c) an isolated nucleic acid molecule that is a reverse complement of the full-length sequence of (a) or (b); and
   (d) an isolated nucleic acid molecule that has at least 95% nucleotide identity to any one of (a)-(c) wherein the nucleic acid molecule encodes a uronate dehydrogenase.

25. An isolated uronate dehydrogenase polypeptide encoded by the vector of claim 24 wherein the uronate dehydrogenase polypeptide is linked to a tag.

26. A isolated cell comprising the recombinant expression vector of claim 24, optionally wherein the isolated cell is a bacterial cell, a fungal cell, a yeast cell, a plant cell, an insect cell, or an animal cell.

27. A method for the production of an uronate dehydrogenase comprising culturing the isolated cell of claim 26 under conditions that permit expression of the uronate dehydrogenase, optionally further comprising recovering the uronate dehydrogenase from the culture medium or the cell.

* * * * *

UNITED STATES PATENT AND TRADEMARK OFFICE
CERTIFICATE OF CORRECTION

PATENT NO. : 8,835,147 B2
APPLICATION NO. : 12/935983
DATED : September 16, 2014
INVENTOR(S) : Tae Seok Moon et al.

It is certified that error appears in the above-identified patent and that said Letters Patent is hereby corrected as shown below:

In the Specification:

Column 1, lines 20-21: "This work was funded in part by the Office of Naval Research under grant number N000140510656" should be replaced to read:

--This invention was made with government support under Grant No. N00014-05-1-0656 awarded by Navy ONR--

Signed and Sealed this
Seventh Day of April, 2015

Michelle K. Lee
*Director of the United States Patent and Trademark Office*